US012605344B2

(12) United States Patent
Pagels et al.

(10) Patent No.: US 12,605,344 B2
(45) **Date of Patent: \*Apr. 21, 2026**

(54) NANOPARTICLES ENCAPSULATING SOLUBLE BIOLOGICS, THERAPEUTICS, AND IMAGING AGENTS

(71) Applicant: The Trustees of Princeton University, Princeton, NJ (US)

(72) Inventors: Robert F. Pagels, Princeton, NJ (US); Robert K. Prud'Homme, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 13 days.

This patent is subject to a terminal disclaimer.

(21) Appl. No.: 18/083,458

(22) Filed: Dec. 16, 2022

(65) Prior Publication Data

US 2023/0126007 A1 Apr. 27, 2023

Related U.S. Application Data

(60) Continuation of application No. 16/253,850, filed on Jan. 22, 2019, now Pat. No. 11,554,101, which is a
(Continued)

(51) Int. Cl.
*A61K 9/51* (2006.01)
*A61K 31/00* (2006.01)
(Continued)

(52) U.S. Cl.
CPC .......... *A61K 9/5138* (2013.01); *A61K 9/5146* (2013.01); *A61K 9/5192* (2013.01);
(Continued)

(58) Field of Classification Search
CPC .................................................. A61K 9/5138
See application file for complete search history.

(56) References Cited

U.S. PATENT DOCUMENTS

| | | | |
|---|---|---|---|
| 1,690,760 A | 11/1928 | Volwiler | |
| 4,342,653 A | 8/1982 | Halverson | |

(Continued)

FOREIGN PATENT DOCUMENTS

| | | | |
|---|---|---|---|
| CN | 100389766 C | 5/2008 | |
| CN | 102334609 A | 2/2012 | |

(Continued)

OTHER PUBLICATIONS

Bin Xu, Hongjing Dou, Ke Tao, Kang Sun, Rong Lu, and Weibin Shi. "Influence of experimental parameters and the copolymer structure on the size control of nanospheres in double emulsion method." Journal of Polymer Research, vol. 18, 2011, pp. 131-137. (Year: 2011).*

(Continued)

*Primary Examiner* — Isaac Shomer
(74) *Attorney, Agent, or Firm* — Nixon & Vanderhye P.C.; Lars H. Genieser

(57) ABSTRACT

An "inverse" precipitation route to precipitate aqueous soluble species with copolymers as nanoparticles having a hydrophilic, polar core and a less polar shell is described.

20 Claims, 6 Drawing Sheets

Specification includes a Sequence Listing.

Related U.S. Application Data division of application No. 15/321,588, filed as application No. PCT/US2015/036060 on Jun. 16, 2015, now Pat. No. 10,231,937.

(60) Provisional application No. 62/016,363, filed on Jun. 24, 2014.

(51) Int. Cl.

| | |
|---|---|
| *A61K 31/405* | (2006.01) |
| *A61K 31/7036* | (2006.01) |
| *A61K 38/06* | (2006.01) |
| *A61K 38/14* | (2006.01) |
| *A61K 38/47* | (2006.01) |
| *C09B 67/02* | (2006.01) |

(52) U.S. Cl.

CPC ............ *A61K 31/00* (2013.01); *A61K 31/405* (2013.01); *A61K 31/7036* (2013.01); *A61K 38/063* (2013.01); *A61K 38/14* (2013.01); *A61K 38/47* (2013.01); *C09B 67/0097* (2013.01); *C12Y 302/01017* (2013.01)

(56) References Cited

U.S. PATENT DOCUMENTS

| | | | |
|---|---|---|---|
| 4,382,982 A | 5/1983 | Whillans | |
| 4,678,516 A | 7/1987 | Alderman et al. | |
| 4,695,464 A | 9/1987 | Alderman | |
| 4,888,238 A | 12/1989 | Katz et al. | |
| 4,999,417 A | 3/1991 | Domb | |
| 5,366,734 A | 11/1994 | Hutchinson | |
| 5,578,325 A | 11/1996 | Domb et al. | |
| 5,851,579 A | 12/1998 | Wu et al. | |
| 6,291,013 B1 | 9/2001 | Gibson et al. | |
| 6,383,500 B1 | 5/2002 | Wooley et al. | |
| 6,610,653 B1 | 8/2003 | Backstrom et al. | |
| 6,730,322 B1 | 5/2004 | Bernstein et al. | |
| 6,998,426 B2 | 2/2006 | L'Alloret | |
| 7,052,719 B2 | 5/2006 | Bernstein | |
| 7,842,308 B2 | 11/2010 | McAllister et al. | |
| 7,977,024 B2 | 7/2011 | Zhou et al. | |
| 8,137,699 B2 | 3/2012 | Johnson et al. | |
| 8,288,001 B1 | 10/2012 | Fan et al. | |
| 8,298,581 B2 | 10/2012 | Fischer et al. | |
| 8,603,514 B2 | 12/2013 | Yang | |
| 8,623,329 B1 | 1/2014 | Hansen et al. | |
| 8,703,196 B2 | 4/2014 | Babcock et al. | |
| 9,504,658 B2 | 11/2016 | Miller et al. | |
| 9,603,830 B2 | 3/2017 | Powell et al. | |
| 9,782,358 B2 | 10/2017 | Kataoka et al. | |
| 10,231,937 B2 * | 3/2019 | Pagels .................... A61K 38/14 |
| 11,103,461 B2 * | 8/2021 | Prud'Homme ...... A61K 9/5031 |
| 11,554,101 B2 * | 1/2023 | Pagels ................. A61K 38/063 |
| 12,186,436 B2 | 1/2025 | Prud'homme et al. | |
| 12,357,582 B2 | 7/2025 | Prud'homme et al. | |
| 2004/0023393 A1 | 2/2004 | Monahan et al. | |
| 2004/0052824 A1 | 3/2004 | Chacra-Vernet | |
| 2004/0091546 A1 | 5/2004 | Johnson et al. | |
| 2004/0236050 A1 | 11/2004 | Lundquist et al. | |
| 2005/0158390 A1 | 7/2005 | Rana et al. | |
| 2005/0228074 A1 | 10/2005 | Warren et al. | |
| 2006/0040831 A1 | 2/2006 | Cassidy et al. | |
| 2006/0057215 A1 | 3/2006 | Raiche et al. | |
| 2006/0078624 A1 | 4/2006 | Zalipsky et al. | |
| 2006/0159921 A1 | 7/2006 | Murthy et al. | |
| 2006/0224095 A1 | 10/2006 | Claverie et al. | |
| 2006/0247383 A1 | 11/2006 | Hedrick et al. | |
| 2007/0042498 A1 | 2/2007 | Ebner | |
| 2007/0231355 A1 | 10/2007 | Quadir et al. | |
| 2008/0145432 A1 | 6/2008 | Kakizawa et al. | |
| 2008/0160305 A1 | 7/2008 | Warren et al. | |
| 2008/0274194 A1 | 11/2008 | Miller et al. | |
| 2009/0061009 A1 | 3/2009 | Schwarz et al. | |

| | | | |
|---|---|---|---|
| 2009/0068743 A1 | 3/2009 | Turnell et al. | |
| 2009/0155326 A1 | 6/2009 | Mack et al. | |
| 2009/0325292 A1 * | 12/2009 | Baker .................... A61K 47/34 |
| | | | 435/375 |
| 2010/0150994 A1 | 6/2010 | Kotyla | |
| 2010/0166866 A1 | 7/2010 | Fischer et al. | |
| 2010/0203149 A1 | 8/2010 | Radosz et al. | |
| 2010/0233251 A1 | 9/2010 | Von Andrian et al. | |
| 2010/0305219 A1 | 12/2010 | Granick et al. | |
| 2010/0310649 A1 | 12/2010 | Richard et al. | |
| 2010/0330368 A1 | 12/2010 | Prud'homme et al. | |
| 2011/0012057 A1 | 1/2011 | Lindner et al. | |
| 2011/0022129 A1 | 1/2011 | Prud'homme et al. | |
| 2011/0064821 A1 | 3/2011 | Catchpole et al. | |
| 2011/0200828 A1 | 8/2011 | Li et al. | |
| 2011/0206739 A1 | 8/2011 | Nicolosi et al. | |
| 2011/0229516 A1 | 9/2011 | Ochomogo et al. | |
| 2011/0236686 A1 * | 9/2011 | Kitano ...................... C08F 8/00 |
| | | | 526/89 |
| 2011/0293701 A1 | 12/2011 | Bratzler et al. | |
| 2012/0009267 A1 | 1/2012 | Cho et al. | |
| 2012/0041150 A1 | 2/2012 | Yabu et al. | |
| 2012/0121510 A1 | 5/2012 | Brem et al. | |
| 2012/0171254 A1 | 7/2012 | Johnson et al. | |
| 2012/0230913 A1 | 9/2012 | Johnston et al. | |
| 2012/0308640 A1 | 12/2012 | Percec et al. | |
| 2013/0064954 A1 | 3/2013 | Ochomogo et al. | |
| 2013/0101516 A1 | 4/2013 | Zhao | |
| 2013/0115272 A1 | 5/2013 | de Fougerolles et al. | |
| 2013/0122058 A1 | 5/2013 | Chow et al. | |
| 2013/0171208 A1 | 7/2013 | Smith et al. | |
| 2013/0337078 A1 | 12/2013 | Mayer et al. | |
| 2014/0037573 A1 | 2/2014 | Eliasof et al. | |
| 2014/0099379 A1 | 4/2014 | Beck-Broichsitter et al. | |
| 2014/0249235 A1 | 9/2014 | Brugel et al. | |
| 2014/0302154 A1 | 10/2014 | Waldoefner et al. | |
| 2014/0356443 A1 | 12/2014 | Brisander et al. | |
| 2015/0086618 A1 | 3/2015 | Onyuksel et al. | |
| 2015/0218198 A1 | 8/2015 | Petermann et al. | |
| 2015/0283218 A1 | 10/2015 | Shea et al. | |
| 2015/0290233 A1 | 10/2015 | Yarden et al. | |
| 2015/0298084 A1 | 10/2015 | Schoeppe et al. | |
| 2015/0299369 A1 | 10/2015 | Ausserre et al. | |
| 2016/0235677 A1 | 8/2016 | Hoerr et al. | |
| 2016/0317459 A1 | 11/2016 | Ensign et al. | |
| 2016/0346266 A1 | 12/2016 | Tolleth et al. | |
| 2017/0042823 A1 | 2/2017 | Prud'Homme et al. | |
| 2017/0151339 A1 | 6/2017 | White et al. | |
| 2017/0209386 A1 | 7/2017 | Pagels et al. | |
| 2018/0009924 A1 | 1/2018 | Sadowski et al. | |
| 2018/0125915 A1 | 5/2018 | Mikhail | |
| 2019/0008788 A1 | 1/2019 | Prud'Homme et al. | |
| 2019/0151252 A1 | 5/2019 | Pagels et al. | |
| 2019/0192444 A1 | 6/2019 | Barzilay et al. | |
| 2020/0023332 A1 | 1/2020 | Prud'homme et al. | |
| 2020/0147032 A1 | 5/2020 | Prud'homme et al. | |
| 2020/0206136 A1 | 7/2020 | Prud'Homme et al. | |
| 2021/0085619 A1 | 3/2021 | Baldwin et al. | |
| 2021/0378980 A1 | 12/2021 | Horhota et al. | |
| 2021/0379181 A1 | 12/2021 | Rauch et al. | |

FOREIGN PATENT DOCUMENTS

| | | | |
|---|---|---|---|
| CN | 104042567 A | 9/2014 | |
| CN | 105213250 A | 1/2016 | |
| CN | 106750272 A | 5/2017 | |
| EP | 2962752 A1 | 1/2016 | |
| JP | 2000514791 A | 11/2000 | |
| JP | 2003513019 A | 4/2003 | |
| JP | 2008297288 A * | 12/2008 | |
| JP | 2011506499 A | 3/2011 | |
| JP | 2014514275 A | 6/2014 | |
| JP | 2014-516045 | 7/2014 | |
| JP | 2015129128 A | 7/2015 | |
| JP | 2015529683 A | 10/2015 | |
| JP | 2017505800 A | 2/2017 | |
| JP | 2018535228 A | 11/2018 | |
| WO | 1994008599 A1 | 4/1994 | |
| WO | 1997049736 A2 | 12/1997 | |

(56) References Cited

FOREIGN PATENT DOCUMENTS

| WO | WO 1997049387 A1 | 12/1997 | |
| WO | 2001022937 A1 | 4/2001 | |
| WO | 2002076441 A1 | 10/2002 | |
| WO | 2002078674 A1 | 10/2002 | |
| WO | WO 2002092069 A1 | 11/2002 | |
| WO | 2009080164 A1 | 7/2009 | |
| WO | WO-2010148653 A1 * | 12/2010 | ........ C08J 3/07 |
| WO | 2012122544 A2 | 9/2012 | |
| WO | 2012160088 | 11/2012 | |
| WO | WO-2013023003 A1 * | 2/2013 | ........ A61K 9/513 |
| WO | 2013160773 A2 | 10/2013 | |
| WO | 2014043625 A1 | 3/2014 | |
| WO | 2014133172 A1 | 9/2014 | |
| WO | 2014165679 A1 | 10/2014 | |
| WO | 2015123562 A1 | 8/2015 | |
| WO | 2015130835 A1 | 9/2015 | |
| WO | 2015200054 A2 | 12/2015 | |
| WO | 2015200054 A9 | 12/2015 | |
| WO | 2016193810 A1 | 12/2016 | |
| WO | 2017089942 A1 | 6/2017 | |
| WO | 2017112828 A1 | 6/2017 | |
| WO | WO 2017130046 A1 | 8/2017 | |
| WO | 2019055539 A1 | 3/2019 | |
| WO | WO 2019/050969 A1 | 3/2019 | |
| WO | 2019090030 A1 | 5/2019 | |
| WO | 2020018890 A1 | 1/2020 | |
| WO | WO 2020/227350 A1 | 11/2020 | |
| WO | WO 2020252346 A1 | 12/2020 | |
| WO | WO 2021/046078 A1 | 3/2021 | |

OTHER PUBLICATIONS

English Translation of JP 2008297288 A. Obtained from https://patents.google.com/patent/JP2008297288A/en?oq=JP+2008297288+ on Feb. 13, 2025, originally published 2008, 8 printed pages. (Year: 2008).*

Kai Qi, Qinggao Ma, Edward E. Remsen, Christopher G. Clark, Jr., and Karen L. Wooley. "Determination of the Bioavailability of Biotin Conjugated onto Shell Cross-Linked (SCK) Nanoparticles." Journal of the American Chemical Society, vol. 126, 2004, pp. 6599-6607. (Year: 2004).*

Naomi Kohen. "Characterization of Polystyrene-block-poly(acrylic acid) Micelles." Thesis, Massachusetts Institute of Technology, Jun. 2005, pp. 1-38. (Year: 2005).*

Olivier Colombani et al. "Structure of Micelles of Poly(n-butyl acrylate)-block-poly(acrylic acid) Diblock Copolymers in Aqueous Solution." Macromolecules, vol. 40, 2007, pp. 4351-4362. (Year: 2007).*

Olivier Colombani et al. "Synthesis of Poly(n-butyl acrylate)-block-poly(acrylic acid) Diblock Copolymers by ATRP and Their Micellization in Water." Macromolecules, vol. 40, 2007, pp. 4338-4350. (Year: 2007).*

Elham Eghbali et al. "Rheology and Phase Behavior of Poly(n-butyl acrylate)-block-poly(acrylic acid) in Aqueous Solution." Langmuir, vol. 22, 2006, pp. 4766-4776. (Year: 2006).*

Byeong-Su Kim and T. Andrew Taton. "Multicomponent Nanoparticles via Self-Assembly with Cross-Linked Block Copolymer Surfactants." Langmuir, vol. 23, 2007, pp. 2198-2202. (Year: 2007).*

Marina Talelli, Matthias Barz, Christianne J.F. Rijcken, Fabian Kiessling, Wim E. Hennink, and Twan Lammers. "Core-crosslinked polymeric micelles: Principles, preparation, biomedical applications and clinical translation." Nano Today, vol. 10, 2015, pp. 93-117. (Year: 2015).*

U.S. Appl. No. 16/517,510 Notice of Allowance and Notice of Allowability dated Nov. 23, 2022.

U.S. Appl. No. 16/816,241 Notice of Allowance and Notice of Allowability dated Nov. 16, 2022.

Erre et al. "Chromium(III) Acetate, Chromium(III) Acetate Hydroxide, or mu3-Oxo-esakis-(mu2-acetato-O,O')-triaqua-trichromium(III) Acetate?", Journal of Chemical Education, (Apr. 1997) vol. 74, No. 4, pp. 432-435.

Liang et al., "Preparation of nanoparticles composed of poly(gamma-glutamic acid)-poly(lactide) block copolymers and evaluation of their uptake by HepG2 cells", Journal of Controlled Release, (2005) vol. 105, pp. 213-225.

Talleli et al., "Core-crosslinked polymeric micelles: Principles, preparation, biomedical applications and clinical translation", Nano Today (2015) vol. 10, pp. 93-117.

U.S. Appl. No. 16/253,850 U.S. Patent & Trademark Office (USPTO) Office Action of Sep. 23, 2021, 23 pages.

U.S. Appl. No. 16/253,850 U.S. Patent & Trademark Office (USPTO) Office Action of Sep. 8, 2020, 23 pages.

U.S. Appl. No. 16/253,850 U.S. Patent & Trademark Office (USPTO) Supplemental Notice of Allowability of Dec. 19, 2022, 2 pages.

U.S. Appl. No. 16/253,850 U.S. Patent & Trademark Office (USPTO) Notice of Allowance & Notice of Allowability of Sep. 13, 2022, 22 pages.

U.S. Appl. No. 16/253,850 U.S. Patent & Trademark Office (USPTO) Notice of Allowance & Notice of Allowability of Apr. 12, 2022, 24 pages.

U.S. Appl. No. 16/253,850 U.S. Patent & Trademark Office (USPTO) Aug. 11, 2021 dated Summary of Interview of Aug. 9, 2021, 3 pages.

U.S. Appl. No. 16/253,850 U.S. Patent & Trademark Office (USPTO) Restriction Requirement of Apr. 7, 2020.

International Preliminary Report on Patentability mailed Mar. 26, 2020 (issued Mar. 17, 2020) in International Application No. PCT/US2018/050714.

U.S. Patent & Trademark Office (USPTO) Office Action dated Sep. 23, 2021 for U.S. Appl. No. 16/253,850.

U.S. Appl. No. 16/761,140 Office Action dated Aug. 26, 2022.

Rädler et al., "Structure of DNA-cationic liposome complexes: DNA intercalation in multilamellar membranes in distinct interhelical packing regimes," Science, vol. 275, No. 5301, pp. 810-814 (1997).

Salentinig et al., "Self-Assembled Structures and pKa Value of Oleic Acid in Systems of Biological Relevance" Langmuir, vol. 26, No. 14, pp. 11670-11679 (2010).

Schwendeman et al., "Injectable controlled release depots for large molecules", Journal of Controlled Release, vol. 190, pp. 240-253 (2014).

Serajuddin, "Salt formation to improve drug solubility" Advanced Drug Delivery Reviews, vol. 59, No. 7, pp. 603-616 (2007).

Shah et al., Poly (glycolic acid-co-DL-lactic acid): diffusion or degradation controlled drug delivery?, Journal of Controlled Release, vol. 18, pp. 261-270 (1992).

Sohn et al., "Polymer prodrug approaches applied to paclitaxel," Polymer Chemistry, vol. 1, No. 6, pp. 778-792 (2010).

Song et al., "A novel in situ hydrophobic ion pairing (HIP) formulation strategy for clinical product selection of a nanoparticle drug delivery system," Journal of Controlled Release, vol. 229, pp. 106-119 (2016).

Turro et al., "Spectroscopic probe analysis of protein-surfactant interactions: the BSA/SDS system," Langmuir, vol. 11, No. 7, pp. 2525-2533 (1995).

U.S. Appl. No. 16/517,510 Notice of Allowance May 9, 2022.

U.S. Appl. No. 16/517,510 Restriction Requirement Mar. 19, 2021.

U.S. Appl. No. 16/517,510 Office Action mailed Sep. 24, 2021.

U.S. Appl. No. 16/761,140 Office Action Feb. 8, 2022.

U.S. Appl. No. 16/761,140 Restriction Requirement of Aug. 19, 2021.

U.S. Appl. No. 16/816,241 Office Action May 12, 2022.

U.S. Appl. No. 16/816,241 Restriction Requirement of Sep. 30, 2021.

Vyavahare et al., "Analysis of Structural Rearrangements of Poly(lactic acid) in the Presence of Water", The Journal of Physical Chemistry B, vol. 118, No. 15, pp. 4185-4193 (2014).

Yu et al., "Nanotechnology for Protein Delivery: Overview and Perspectives", J. Control. Release, vol. 240, pp. 24-37 (2016).

Zhang et al., "Development of Nanoparticles for Antimicrobial Drug Delivery" Current Medicinal Chemistry, vol. 17, No. 6, pp. 585-594 (2010).

Tang et al., "An innovative method for preparation of hydrophobic ion-pairing colistin entrapped poly(lactic acid) nanoparticles: Load-

(56)          References Cited

OTHER PUBLICATIONS ing and release mechanism study", European J. Pharmaceutical Sciences, vol. 102, pp. 63-70 (2017).

Anton et al., "Aqueous-Core Lipid Nanocapsules for Encapsulating Fragile Hydrophilic and/or Lipophilic Molecules," Langmuir, vol. 25, No. 19, pp. 11413-11419 (2009).

Bilati et al., "Development of a nanoprecipitation method intended for the entrapment of hydrophilic drugs into nanoparticles", European J. Pharmaceutical Sciences, vol. 24, pp. 67-75 (2005).

Arshady, "Preparation of biodegradable microspheres and microcapsules: 2. Polyactides and related polyesters", Journal of Controlled Release, vol. 17, pp. 1-22, (1991).

Bilati et al., "Nanoprecipitation Versus Emulsion-based Techniques for the Encapsulation of Proteins Into Biodegradable Nanoparticles and Process-related Stability Issues", AAPS PharmSciTech, vol. 6, No. 4, Article 74, pp. E594-E604 (2005).

Bontha et al., "Polymer micelles with cross-linked ionic cores for delivery of anticancer drugs", Journal of Controlled Release, vol. 114, pp. 163-174 (2006).

Bronich et al., "Polymer Micelle with Cross-Linked Ionic Core", J. Am. Chem Soc., vol. 127, pp. 8236-8237 (2005).

Bronich et al., "Soluble Complexes from Poly(ethylene oxide)-block-polymethacrylate Anions and N-Alkylpyridinium Cations", Macromolecules, vol. 30, pp. 3519-3525 (1997).

D'Addio et al., "Controlling drug nanoparticle formation by rapid precipitation", Advanced Drug Delivery Reviews, vol. 63, pp. 417-426 (2011).

Extended European Search Report (EESR) issued Jan. 8, 2018 in European Application No. 15811879.4.

Gao et al., "Core Cross-Linked Reverse Micelles from Star-Shaped Polymers," Chemistry of Materials, vol. 20, pp. 3063-3067 (2008).

Holland et al., "Polymers for Biodegradable Medical Devices, 1. The Potential of Polyesters As Controlled by Macromolecular Release Systems", Journal of Controlled Release, vol. 4, pp. 155-180 (1986).

Deng et al., "Janus Nanoparticles of Block Copolymers by Emulsion Solvent Evaporation Induced Assembly," Macromolecules, vol. 49, pp. 1362-1368 (2016).

Foerster et al., "Amphiphilic Block Copolymers in Structure-Controlled Nanomaterial Hybrids", Advanced Materials, vol. 10, No. 3, pp. 195-217 (1998).

Google Scholar NPL search string—downloaded Apr. 29, 2020, 1 page.

Groeschel et al., "Guided hierarchical co-assembly of soft patchy nanoparticles", Nature, vol. 503, pp. 247-251 (5 pages & 11 pages Methods, Extended Data Figures 1-9, & Extended Data Table 1) (Nov. 14, 2013).

Guo et al., "Binding of dihydromyricetin and its metal ion complexes with bovine serum albumin", Biotechnology & Biotechnological Equipment, vol. 28, No. 2, pp. 333-341 (2014).

Guo et al., "Synthesis of dihydromyricetin-manganese (II) complex and interaction with DNA", J. Molecular Structure, vol. 1027, pp. 64-69 (2012).

International Search Report and Written Opinion mailed Dec. 6, 2018 in International Application No. PCT/US2018/050714.

International Search Report and Written Opinion mailed Jan. 15, 2019 in International Application No. PCT/US2018/049580.

International Search Report and Written Opinion mailed Feb. 22, 2019 in International Application No. PCT/US2018/058869.

International Search Report and Written Opinion mailed Nov. 22, 2019 in International Application No. PCT/US2019/042574.

Int'l Search Report and Written Opinion mailed Jul. 16, 2015 in Int'l Application No. PCT/US2015/017590.

Int'l Search Report and Written Opinion mailed Sep. 18, 2015 in Int'l Application PCT/US2015/036060.

Int'l Search Report and Written Opinion mailed Mar. 23, 2017 in Int'l Application No. PCT/US2016/068145.

Int'l Search Report and Written Opinion mailed Jan. 26, 2018 in Int'l Application No. PCT/US2017/054779.

IQQueryQuickExport search results—202004301516 (IP.com NPL search results)—downloaded Apr. 30, 2020, 4 pages.

IQQueryQuickExport search results—202004301547 (IP.com NPL search results)—downloaded Apr. 30, 2020, 2 pages.

IQQueryQuickExport search results—202004301605 (IP.com NPL search results)—downloaded Apr. 30, 2020, 5 pages.

IQQueryQuickExport search results—202004301643 (IP.com NPL search results)—downloaded Apr. 30, 2020, 5 pages.

IQQueryQuickExport search results—202004301659 (IP.com NPL search results)—downloaded Apr. 30, 2020, 5 pages.

IQQueryQuickExport search results—202004301700 (IP.com NPL search results)—downloaded Apr. 30, 2020, 2 pages.

Jang et al., "Bicontinuous Block Copolymer Morphologies Produced by Interfacially Active, Thermally Stable Nanoparticles", Macromols., vol. 44, pp. 9366-9373 (2011).

Jang et al., "Synthesis of thermally stable Au-core/Pt-shell nanoparticles and their segregation behavior in diblock copolymer mixtures", Soft Matter, vol. 7, pp. 6255-6263 (2011), doi: 10.1039/clsm05223c.

Jeon et al., "Cooperative Assembly of Block Copolymers with Deformable Interfaces: Toward Nanostructured Particles", Advanced Materials, vol. 20, pp. 4103-4108 (2008), doi: 10.1002/adma.200801377.

Johnson et al., "Nanoprecipitation of organic actives using mixing and block copolymer stabilization", Abstracts of Papers of the American Chemical Society, No. 186 (Abstract) (Sep. 2003).

Johnson et al., "Characterization and Suitability of Therapeutic Antibody Dense Phases for Subcutaneous Delivery", Molecular Pharmaceutics, vol. 10, pp. 3582-3591 (2013).

Johnson et al., "Chemical Processing and Micromixing in Confined Impinging Jets", AIChE Journal, vol. 49, No. 9, pp. 2264-2282 (2003).

Johnston et al., "Concentrated Dispersions of Equilibrium Protein Nanoclusters That Reversibly Dissociate into Active Monomers", ACS Nano, vol. 6, No. 2, pp. 1357-1369 (2012).

Kakizawa et al., "Controlled release of protein drugs from newly developed amphiphilic polymer-based microparticles composed of nanoparticles", Journal of Controlled Release, vol. 142, pp. 8-13 (2010).

Kang et al., "Pore Closing and Opening in Biodegradable Polymers and Their Effect on the Controlled Release of Proteins", Mol. Pharmaceutics, vol. 4, No. 1, pp. 104-118 (2007).

Kim et al., "Critical effect of freezing/freeze-drying on sustained release of FITC-dextran encapsulated within PLGA microspheres", Int'l J. Pharmaceutics, vol. 271, pp. 207-214 (2004).

Kumar et al., "Amphiphilic Janus particles at fluid interfaces", Soft Matter, vol. 9, pp. 6604-6617 (2013).

Lavasanifar et al., "Poly(ethylene oxide)-block-poly(L-amino acid) micelles for drug delivery", Advanced Drug Delivery Reviews, vol. 54, pp. 169-190 (2002).

Liu et al., "CFD Predictions for Chemical Processing in a Confined Impinging-Jets Reactor", AIChE Journal, vol. 52, No. 2, pp. 731-744 (Feb. 2006).

Liu et al., "Mixing in a multi-inlet vortex mixer (MIVM) for flash nano-precipitation", Chemical Engineering Science, vol. 63, pp. 2829-2842 (2008).

Mitragotri et al. "Overcoming the challenges in administering biopharmaceuticals: formulation and delivery strategies", Nat. Rev. Drug Discov., vol. 13, No. 9, pp. 655-672 (Sep. 2014).

Okuyama et al., "Preparation of functional nanostructured particles by spray drying", Advanced Powder Technol., vol. 17, No. 6, pp. 587-611 (2006).

O'Reilly et al., "Cross-linked block copolymer micelles: functional nanostructures of great potential and versatility", Chemical Society Reviews, vol. 35, pp. 1068-1083 (2006).

Liu et al., "Janus Colloids Formed by Biphasic Grafting at a Pickering Emulsion Interface", Angew. Chem., vol. 120, pp. 4037-4039 (2008).

Mai et al., "Controlled Incorporation of Particles into the Central Portion of Vesicle Walls", J. Am. Chem. Soc., vol. 132, pp. 10078-10084 (2010).

Aggarwal et al., "What's fueling the biotech engine—2012 to 2013", Nat. Biotechnol., vol. 32, No. 1, pp. 32-39, Jan. 2014.

(56)             References Cited

OTHER PUBLICATIONS

Ansell et al., "Modulating the Therapeutic Activity of Nanoparticle Delivered Paclitaxel by Manipulating the Hydrophobicity of Prodrug Conjugates," Journal of Medicinal Chemistry, vol. 51, No. 11, pp. 3288-3296 (2008).

Antonietti et al, "Polyelectrolyte-Surfactant Complexes: A New Type of Solid, Mesomorphous Material," Macromolecules, vol. 27, No. 21, pp. 6007-6011 (1994).

Antonov et al., "Entering and exiting the protein?polyelectrolyte coacervate phase via nonmonotonic salt dependence of critical conditions," Biomacromolecules, vol. 11, No. 1, pp. 51-59 (2010).

Bruno et al., Basics and recent advances in peptide and protein drug delivery, Therapeutic Delivery, vol. 4, No. 11, pp. 1443-1467 (2013).

Crater et al., "Barrier Properties of Gastrointestinal Mucus to Nanoparticle Transport," Macromolecular Bioscience, vol. 10, No. 12, pp. 1473-1483 (2010).

Cu et al., "Drug delivery: Stealth particles give mucus the slip," Nature Materials, vol. 8, No. 1, pp. 11-13 (2009).

Davies et al., "Recent advances in the management of cystic fibrosis," Archives of Disease in Childhood, vol. 99, No. 11, pp. 1033-1036 (2014).

Ensign et al., "Oral drug delivery with polymeric nanoparticles: The gastrointestinal mucus barriers," Advanced Drug Delivery Reviews, vol. 64, No. 6, pp. 557-570 (2012).

Galindo-Rodriguez et al., "Polymeric nanoparticles for oral delivery of drugs and vaccines: a critical evaluation of in vivo studies," Critical Reviews in Therapeutic Drug Carrier Systems, vol. 22, No. 5, pp. 419-464 (2005).

Gaudana et al., "Design and evaluation of a novel nanoparticulate-based formulation encapsulating a HIP complex of lysozyme," Pharmaceutical Development and Technology, vol. 18, No. 3, pp. 752-759 (2013).

Gindy et al., "Mechanism of macromolecular structure evolution in self-assembled lipid nanoparticles for siRNA delivery," Langmuir, vol. 30, No. 16, pp. 4613-4622 (2014).

Gregory et al., "Adsorption and flocculation by polymers and polymer mixtures", Advances in Colloid and Interface Science, vol. 169, No. 1, pp. 1-12 (2011).

Horigome, et al., "Long-Time Relaxation of Suspensions Flocculated by Associating Polymers", Langmuir, vol. 18, No. 6, pp. 1968-1973 (2002).

Høiby, N., "Recent advances in the treatment of Pseudomonas aeruginosa infections in cystic fibrosis" BMC Medicine, vol. 9, No. 32, pp. 1-7 (2011).

Ilton et al., "Direct Measurement of the Critical Pore Size in a Model Membrane", Physical Review Letters, vol. 117, Issue 25, pp. 257801-1-257801-5 (Dec. 2016).

Immordino et al., "Stealth liposomes: review of the basic science, rationale, and clinical applications, existing and potential," International Journal of Nanomedicine, vol. 1, No. 3, pp. 297-315 (2006).

International Preliminary Report on Patentability issued Mar. 26, 2020 in International Application No. PCT/US2018/050714.

International Search Report and Written Opinion issued Feb. 22, 2019 in International Application No. PCT/US2018/058869.

International Search Report and Written Opinion issued Dec. 6, 2018 in International Application No. PCT/US2018/050714.

Jain et al., "Peptide and Protein Delivery Using New Drug Delivery Systems," Crit. Rev. Ther. Drug Carrier Syst., vol. 30, No. 4, pp. 293-329 (2013).

Johnson et al., "Flash NanoPrecipitation of Organic Actives and Block Copolymers using a Confined Impinging Jets Mixer," Australian Journal of Chemistry, vol. 56, No. 10, pp. 1021-1024 (2003).

Khanvilkar et al., "Drug transfer through mucus," Advanced Drug Delivery Reviews, vol. 48, Nos. 2-3, pp. 173-193 (2001).

Kovalainen et al., "Novel Delivery Systems for Improving the Clinical Use of Peptides", Pharmacol. Rev., vol. 67, No. 3, pp. 541-561 (Jul. 2015).

Lai et al., "Mucus-penetrating nanoparticles for drug and gene delivery to mucosal tissues," Advanced Drug Delivery Reviews, vol. 61, No. 2, pp. 158-171 (2009).

Lai et al., "Rapid transport of large polymeric nanoparticles in fresh undiluted human mucus," Proceedings of the National Academy of Sciences, vol. 104, No. 5, pp. 1482-1487 (2007).

Langer, "Drug delivery and targeting," Nature, vol. 392, No. 6679, pp. 5-10 (1998).

Li et al., "Pharmacokinetics and Biodistribution of Nanoparticles," Molecular Pharmaceutics, vol. 5, No. 4, pp. 496-504 (2008).

Liu et al., "Ostwald Ripening of beta-Carotene Nanoparticles," Phys. Rev. Lett., vol. 98, No. 3, pp. 036102-1-036102-4 (2007).

Livraghi et al., "Cystic Fibrosis and Other Respiratory Diseases of Impaired Mucus Clearance," Toxicologic Pathology, vol. 35, No. 1, pp. 116-129 (2007).

Lu et al., "Hydrophobic Ion Pairing of Peptide Antibiotics for Processing into Controlled Release Nanocarrier Formulations", Molecular Pharmaceutics, vol. 15, No. 1, pp. 216-225 (2018).

Luo et al., "Synthetic DNA delivery systems," Nature Biotechnology, vol. 18, No. 1, pp. 33-37 (2000).

Marcus et al., "Ion Pairing," Chemical Reviews, vol. 106, No. 11, pp. 4585-4621 (2006).

Markwalter et al., "Inverse Flash NanoPrecipitation for Biologics Encapsulation: Understanding Process Losses via an Extraction Protocol", Control of Amphiphile Self-Assembling at the Molecular Level: Supra-Molecular Assemblies with Tuned Physicochemical Properties for Delivery Applications, pp. 275-296 (Jan. 1, 2017).

Matschiner et al., "Optimization of topical erythromycin formulations by ion pairing," Skin Pharmacology: The Official Journal of the Skin Pharmacology Society, vol. 8, No. 6, pp. 319-325 (1995).

Meyer et al. "Hydrophobic Ion Pairing: Altering the Solubility Properties of Biomolecules," Pharmaceutical Research, vol. 15, No. 2, pp. 188-193 (1998).

Muehle et al., "Stability of Particle Aggregates in Flocculation with Polymers: Stabilität von Teilchenaggregaten bei der Flockung mit Polymeren", Chemical Engineering and Processing: Process Intensification, vol. 29, No. 1, pp. 1-8 (1991).

Mueller et al., "Solid lipid nanoparticles (SLN) for controlled drug delivery—a review of the state of the art," European Journal of Pharmaceutics and Biopharmaceutics, vol. 50, No. 1, pp. 161-177 (2000).

Muheem et al., "A review on the strategies for oral delivery of proteins and peptides and their clinical perspectives," Saudi Pharmaceutical Journal, vol. 24, No. 4, pp. 413-428 (2016).

Notice of Allowance mailed Apr. 12, 2022 in U.S. Appl. No. 16/253,850.

Overbeek et al., "Phase separation in polyelectrolyte solutions. Theory of complex coacervation," Journal of Cellular Physiology, vol. 49, No. S1, pp. 7-26 (1957).

Owens et al., "Opsonization, biodistribution, and pharmacokinetics of polymeric nanoparticles," International Journal of Pharmaceutics, vol. 307, No. 1, pp. 93-102 (2006).

Pagels et al., "Inverse Flash NanoPrecipitation for Biologics Encapsulation: Nanoparticle Formation and Ionic Stabilization in Organic Solvents", ACS Symp. Ser. 1271, pp. 249-274 (2017).

Patel et al., "A novel approach for antibody nanocarriers development through hydrophobic ion-pairing complexation" Journal of Microencapsulation, vol. 31, No. 6, pp. 542-550 (2014).

Pattni et al., "New Developments in Liposomal Drug Delivery," Chemical Reviews, vol. 115, No. 19, pp. 10938-10966 (2015).

Pham et al., "Micellar Solutions of Associative Triblock Copolymers: Entropic Attraction and Gas-Liquid Transition", Macromolecules, vol. 32, No. 9, pp. 2996-3005 (1999).

Pinkerton et al., "Formation of stable nanocarriers by in situ ion pairing during block-copolymer directed rapid precipitation," Molecular Pharmaceutics, vol. 10, No. 1, pp. 319-328 (2013).

Pustulka, K.M et al., Flash Nanoprecipitation: Particle Structure and Stability, Mol. Pharmaceutics, 10, 4367-4377 (2013).

Reinhold et al., "Self-healing Microencapsulation of Biomacromolecules without Organic Solvents", Angew. Chem. Int. Ed. Engl., vol. 51, No. 43, pp. 10800-10803 (2012).

(56)                    References Cited

OTHER PUBLICATIONS

Reinhold et al., "Self-Healing Microencapsulation of Biomacromolecules without Organic Solvents", Angewandte Chemie, vol. 124, Issue 43, pp. 10958-10961 (2012).
Pagels et al., "Polymeric nanoparticles and microparticles for the delivery of peptides, biologics, and soluble therapeutics," Journal of Controlled Release, vol. 219, pp. 519-535 (2015).
Patil et al., "Retention of trypsin activity in spermine alginate microcapsules", Journal of Microencapsulation, vol. 14, No. 4, pp. 469-474 (1997).
Peters et al., "Biotech Products in Big Pharma Clinical Pipelines Have Grown Dramatically According to the Tufts Center for the Study of Drug Development", Nov. 14, 2013, https://www.biospace.com/...a-clinical-pipelines-have-grown-dramatically-according-to-the-tufts-center-for-the-study-of-drug-development-/, accessed Aug. 29, 2018 (5 pages).
Pitt, "The controlled parenteral delivery of polypeptides and proteins", International Journal of Pharmaceutics, vol. 59, pp. 173-196 (1990).
Prud'Homme et al., "Process for Encapsulating Soluble Biologics Therapeutics, and Imaging Agents", U.S. Appl. No. 16/064,935, filed Jun. 21, 2018.
Pustulka et al., "Flash Nanoprecipitation: Particle Structure and Stability," Molecular Pharmaceutics, vol. 10, pp. 4367-4377 (2013).
Riess et al.,"Emulsifying Properties of Block Copolymers. Oil-Water Emulsions and Microemulsions", Polym. Eng. Sci., vol. 17, No. 8, pp. 634-638 (1977).
Saad et al., "Principles of nanoparticle formation by Flash Nanoprecipitation", Nano Today, vol. 11, No. 2, pp. 212-227 (2016), http://dx.doi.org/10.1016/j.nantod.2016.04.006.
Sahoo et al., "Characterization of Porous PLGA/PLA Microparticles as a Scaffold for Three Dimensional Growth of Breast Cancer Cells", Biomacromolecules, vol. 6, pp. 1132-1139 (2005).
Sato et al., "Therapeutic peptides: technological advances driving peptides into development", Current Opinion in Biotechnology, vol. 17, pp. 638-642 (2006).
Solaro et al., "Targeted Delivery of Protein Drugs by Nanocarriers", Materials, vol. 3, No. 3, pp. 1928-1980 (2010).
Sosa et al., "Soft Multifaced and Patchy Colloids by Constrained Volume Self-Assembly", Macromolecules, vol. 49, pp. 3580-3585 (2016).
Steichen et al., "A review of current nanoparticle and targeting moieties for the delivery of cancer therapeutics", European J. Pharmaceutical Sciences, vol. 48, pp. 416-427 (2013).
U.S. Patent & Trademark Office (USPTO) Office Action dated May 12, 2021 for U.S. Appl. No. 16/810,710.
U.S. Appl. No. 15/321,588 Notice of Allowance of Oct. 24, 2018.
U.S. Appl. No. 15/321,588 Office Action of Apr. 10, 2018.
U.S. Appl. No. 15/321,588 Restriction Requirement of Dec. 1, 2017.
U.S. Appl. No. 15/321,588 Summary of Examiner Interview of Oct. 9, 2018.
U.S. Appl. No. 16/064,935 Notice of Allowance of Aug. 2, 2021.
U.S. Appl. No. 16/064,935 Notice of Allowance of Jun. 21, 2021.
U.S. Appl. No. 16/064,935 Notice of Allowance of Oct. 21, 2020.
U.S. Appl. No. 16/064,935 Notice of Allowance of Apr. 28, 2021.
U.S. Appl. No. 16/064,935 Notice of Allowance of May 6, 2020.
U.S. Appl. No. 16/064,935 Requirement for Restriction/Election of Jan. 13, 2020.
Wang et al., "Characterization of the initial burst release of a model peptide from poly(D,L-lactide-co-glycolide) microspheres", J. Controlled Release, vol. 82, pp. 289-307 (2002).
Xu et al., "Scalable method to produce biodegradable nanoparticles that rapidly penetrate human mucus", Journal of Controlled Release, vol. 170, pp. 279-286 (2013).
Zandonella, "Bob Prud'homme—Flash NanoPrecipitation" http://research.princeton.edu/news/features/a/index.xml?id=6234, accessed Mar. 9, 2018, originally published Dec. 9, 2011, 2 printed pages.

Zhang et al., "Amphiphilic cylindrical brushes with poly(acrylic acid) core and poly(n-butyl acrylate) shell and narrow length distribution", Polymer, vol. 44, pp. 1449-1458 (2003).
Zhu et al., "Preparation and characterization of hCG-loaded polylactide or poly(lactide-co-glycolide) microspheres using a modified water-in-oil-in-water (w/o/w) emulsion solvent evaporation technique," J. Microencapsulation, vol. 18, No. 2, pp. 247-260 (2001).
U.S. Appl. No. 17/260,640 Office Action dated Oct. 30, 2023.
U.S. Appl. No. 17/260,640 Notice of Allowance & Notice of Allowability dated Mar. 13, 2024.
U.S. Appl. No. 17/260,640 Notice of Allowance & Notice of Allowability dated Aug. 16, 2024.
U.S. Appl. No. 17/260,640 Corrected Notice of Allowability dated Nov. 20, 2024.
U.S. Appl. No. 17/260,640 Interview Summary dated Mar. 13, 2024 for Examiner Interview of Feb. 29, 2024.
U.S. Appl. No. 17/260,640 Interview Summary dated Apr. 12, 2024 for Examiner Interview of Feb. 29, 2024.
U.S. Appl. No. 17/260,640 Interview Summary dated Jul. 9, 2024 for Examiner Interview of Jun. 13, 2024.
U.S. Appl. No. 16/761,140 Notice of Allowance & Notice of Allowability dated Nov. 14, 2024.
U.S. Appl. No. 16/761,140 Interview Summary dated Nov. 14, 2024 for Examiner Interview of Oct. 30, 2024.
U.S. Appl. No. 16/517,510 Notice of Allowance & Notice of Allowability dated Apr. 19, 2023.
U.S. Appl. No. 16/761,140 Office Action dated Feb. 14, 2024.
U.S. Appl. No. 16/761,140 Office Action dated Jun. 5, 2023.
U.S. Appl. No. 16/816,241 Notice of Allowance & Notice of Allowability dated Mar. 7, 2023.
U.S. Appl. No. 16/816,241 Notice of Allowance & Notice of Allowability dated Apr. 13, 2023.
U.S. Appl. No. 16/810,710 Restriction/Election Requirement dated Jan. 6, 2021.
U.S. Appl. No. 16/810,710 Office Action dated Mar. 30, 2022.
U.S. Appl. No. 17/899,157 Restriction/Election Requirement dated Oct. 30, 2023.
U.S. Appl. No. 17/899,157 Office Action dated Apr. 10, 2024.
Hadinoto et al., "Lipid-polymer hybrid nanoparticles as a new generation therapeutic delivery platform: A review", European Journal of Pharmaceutics & Biopharmaceutics, vol. 85, No. 3, part A, pp. 427-443 (2013).
International Patent Application PCT/US2020/031579 International Search Report and Written Opinion dated Aug. 3, 2020.
International Patent Application PCT/US2020/037542 International Search Report and Written Opinion dated Sep. 11, 2020.
International Patent Application PCT/US2020/048986 International Search Report and Written Opinion dated Feb. 16, 2021.
Johnson et al., "Engineering the Direct Precipitation of Stabilized Organic and Block Copolymer Nonparticles as Unique Composites", Abstracts of Papers of the American Chemical Society, No. 441 (Abstract) (Sep. 2003).
Kauffman et al., "Materials for non-viral intracellular delivery of messenger RNA therapeutics", J. Controlled Release, vol. 240, pp. 227-234 (2016).
Savjani, K.T. et al., "Drug Solubility: Importance and Enhancement Techniques", ISRN Pharmaceutics, vol. 2012, Article ID 195727, pp. 1-10 (2012).
Sheela, D.L. et al., "Laurie acid induce cell death in colon cancer cells mediated by the epidermal growth factor receptor downregulation: An in silica and in vitro study", Human & Experimental Toxicology, (Epub. Apr. 3, 2019) □pp. 1-9, DOI: 10.1177/0960327119839185.
Babu, N.J. & Nangia, A, "Solubility Advantage of Amorphous Drugs and Pharmaceutical Cocrystals", Crystal Growth & Design, vol. 11, pp. 2662-2679 (2011).
Bailly, N. et al. "Poly(N-vinylpyrrolidone)-block-poly(vinyl acetate) as a Drug Delivery Vehicle for Hydrophobic Drugs", Biomacromolecules, vol. 13, pp. 4109-4117 (2012).
BASF, Luviscol VA Grades Technical Information, Jun. 2012, pp. 1-14.

(56)  References Cited

OTHER PUBLICATIONS

"The Complete Guide to Enteric Coating", https://astenzymes.com/the-complete-guide-to-enteric-coating/, pp. 1-11, accessed Aug. 11, 2020.

"Enteric Coating—The Enteric Coating Process", https://www.xtend-life.com/pages/enteric-coating, pp. 1-6, accessed Aug. 12, 2020.

Etchenausia, L. et al., "RAFT/MADIX emulsion copolymerization of vinyl acetate and N-vinylcaprolactam: towards waterborne physically crosslinked thermoresponsive particles", Polymer Chemistry, DOI: 10.1039/C7PY00221A, pp. 1-28 (2017).

Guo, Q. et al., "Biosynthesis of gold nanoparticles using a kind of flavanol: Dihydromyricetin", Colloids & Surfaces A: Physicochem. & Engineering Aspects, vol. 441, pp. 127-132 (2014).

* cited by examiner

NANOPARTICLES ENCAPSULATING SOLUBLE BIOLOGICS, THERAPEUTICS, AND IMAGING AGENTS

This application is a continuation of prior application Ser. No. 16/253,850, filed Jan. 22, 2019 (published as U.S. Patent Application Publication No. US 2019-0151252 A1 on May 23, 2019), which is a division of prior application Ser. No. 15/321,588, filed Dec. 22, 2016 (published as U.S. Patent Application Publication No. US 2017-0209386 A1 on Jul. 27, 2017), which is a National Stage of International Application No. PCT/US2015/036060, filed Jun. 16, 2015 (published as International Application Publication No. WO/2015/200054 on Dec. 30, 2015), which claims the benefit of U.S. Provisional Application No. 62/016,363, filed Jun. 24, 2014, all of which are hereby incorporated by reference in their entireties herein.

Incorporated by reference is the file 8857-6065_ST26_SequenceListing.xml, which was created on Dec. 2, 2025 and has a size of 2,161 bytes.

FIELD OF THE INVENTION

The present invention relates to a process of making nanoparticles having a hydrophilic core.

BACKGROUND OF THE INVENTION

Protein and peptide therapeutics are a growing segment of the pharmaceutical marketplace. In eleven years, from 2001 to 2012, the global sales of pharmaceutical biologic therapeutics (biologics) more than tripled from $36 billion to $163 billion. In that same period, revenue generated by biologics within the top 10 selling pharmaceuticals increased from 7% to 71% (S. Peters, Biotech Products in Big Pharma Clinical Pipelines Have Grown Dramatically, Tufts CSDD Impact Report. 15 (2013) 1). Their specificity makes them ideal therapeutics for the treatment of a variety of diseases including cancer and AIDS. This specificity comes as a result of structural complexity, which is a strength of biologics for use as therapeutics and a challenge in trying to formulate and deliver them (S. Mitragotri, P. A. Burke, R. Langer, Overcoming the challenges in administering biopharmaceuticals: formulation and delivery strategies, Nat Rev Drug Discov. 13 (2014) 655-672).

While humanized antibodies may be long circulating, proteins and peptides can be cleared from the bloodstream in a matter of minutes either due to renal clearance or enzymatic degradation (A. K. Sato, M. Viswanathan, R. B. Kent, C. R. Wood, Therapeutic peptides: technological advances driving peptides into development, Curr. Opin. Biotechnol. 17 (2006) 638-642). Therefore, delivery and extended release can require encapsulation of the biologic into nanocarriers (NCs) or microcarriers (MCs). NCs can be defined as having sizes below 400 nm, making them prospects for injectable formulations, and MCs can be defined as having sizes above 1-10 microns, so that they are appropriate for depot delivery. Requirements of NCs and MCs are high loading, high encapsulation efficiency, and an appropriate release profile of the biologic therapeutic.

The term "biologic" can encompass a range of therapeutics including peptides, oligonucleotides, polypeptides, polypeptide antibiotics, proteins, and antibodies. For example, a peptide may include a sequence of 1 to 40 amino acids. While there have been recent promising advances in oral delivery of biologics, the difficulty in translocating NCs through mucus layers and across the GI (gastrointestinal) tract epithelial layer makes this a less developed area than parenteral administration. However, the principles for NC formulation apply equally to oral or parenteral NCs. Examples of carriers include hydrogel carriers composed of water soluble polymers and non-swellable carriers composed of hydrophobic or solid matrices.

SUMMARY

A method of the invention for encapsulating water soluble molecules using rapid, controlled precipitation is presented. Water soluble molecules—including peptides, proteins, DNA, RNA, non-biologic therapeutics, polysaccharide-based therapeutics (e.g., tobramycin) and imaging agents—precipitate into nanoparticles that are protected by a copolymer stabilizing agent. These particles may be covalently or non-covalently stabilized. The particles may be coated with an amphiphilic polymer, or processed into microparticles or larger monoliths. Post processing on the final construct may conducted.

A method of the invention for encapsulating a water soluble agent includes dissolving the water soluble agent and a copolymer in a polar process solvent to form a first process solution. The first process solution can be continuously mixed with a nonprocess solvent to form a mixed solution from which a nanoparticle assembles and precipitates. The copolymer can include at least one region that is more polar and at least one region that is less polar. The nonprocess solvent is or must be less polar than the polar process solvent. The nanoparticle can include a core and a shell. The core can include the more polar region of the copolymer and the water soluble agent. The shell can include the less polar region of the copolymer. The mixing can cause no more than 20 percent by volume of the polar process solvent to phase separate.

In a method of the invention, the water soluble agent can be a biologic material, an amino acid, a peptide, a protein, DNA, RNA, a saccharide, glutathione, tryptophan, a lysozyme, glucagon-like peptide-1 (GLP-1), a small molecule therapeutic, tobramycin, vancomycin, an imaging agent, eosin Y, tartrazine, a metal chelate, a gadolinium chelate, gadolinium diethylene triamine pentaacetic acid (GD-DTPA), or combinations.

For example, the copolymer can be a random copolymer, a block copolymer, a diblock copolymer, a triblock copolymer, a multiblock copolymer, or a branched-comb copolymer. For example, the copolymer can include at least one more polar region (region that is more polar). The at least one more polar region of the copolymer can include at least one anionic more polar region. For example, this anionic more polar region can include anionic residues (units or monomers), poly(acrylic acid) (PAA), hyaluronic acid, poly (glutamic acid), poly(aspartic acid), or combinations.

For example, the at least one more polar region of the copolymer can include at least one cationic more polar region. For example, this cationic more polar region may include cationic residues, such as chitosan polymer domains, histadine lipids, histamines, spermadines, polyethylene-imines, or combinations. For example, the copolymer can include at least one less polar region (region that is less polar) that includes poly(n-butyl acrylate) (PBA), poly(lactic acid) (PLA), poly(caprolactone) (PCL), poly(lactic-co-glycolic acid) (PLGA), lipid or phospholipid grafted units, or cholesterol grafted units, or combinations. For example, the copolymer can be poly(acrylic acid)-block-poly(n-butyl acrylate) (PAA-b-PBA).

In a method of the invention, the polar process solvent can be water, an alcohol, methanol, ethanol, acetone, acetonitrile, dimethyl sulfoxide (DMSO), dimethylformamide (DMF), N-methyl pyrrolidone (NMP), or combinations.

In a method of the invention, the nonprocess solvent can be chloroform, dichloromethane, an alkane, hexane, an ether, diethyl ether, tetrahydrofuran (THF), toluene, acetone, or combinations. For example, the nonprocess solvent can be chloroform, acetone, or combinations. For example, the polar process solvent and the nonprocess solvent can be miscible.

In a method of the invention, a time of mixing of the process solution with the nonprocess solvent is less than an assembly time of the nanoparticle. For example, the water soluble agent and the copolymer can have a supersaturation level in the solution ranging from 10 to 10,000. For example, the nanoparticle can have a size ranging from about 40 nm to about 400 nm.

A method of the invention includes stabilizing the nanoparticle core through crosslinking of the copolymer. For example, the nanoparticle can be crosslinked during assembly of the nanoparticle. For example, the nanoparticle can be crosslinked after assembly of the nanoparticle. The crosslinking can be covalent crosslinking. The crosslinking can be non-covalent, ionic, chelation, acid-base, or hydrogen bonding crosslinking.

A crosslinking agent can be added to crosslink the copolymer. For example, the crosslinking agent can be added to crosslink a portion of the copolymer of anionic functionality. For example, the crosslinking agent can be an alkaline earth halide, a magnesium halide, magnesium chloride, a calcium halide, calcium chloride, a transition metal halide, an iron halide, iron(III) chloride, spermine, or combinations. For example, the crosslinking agent can be a metal acetate, an alkaline earth acetate, a transition metal acetate, calcium acetate, or combinations. For example, the crosslinking agent can be chromium(III) acetate, or another chromium (III) salt. For example, the water soluble agent can include tobramycin and the tobramycin can crosslink the copolymer. Other bio-compatible multi-cationic water soluble agents may be used as crosslinking agents, for example, to crosslink anionic sections of the copolymer.

If the polar agent includes cationic functional groups, then crosslinking may be achieved by the addition of polyanionic components. Examples of these are poly(acrylic acid) (PAA), hyaluronic acid, poly(glutamic acid), poly (aspartic acid), citric acid, polycitric acid, anionic oligonucleotides, and multi-valent anions.

A method of the invention includes coating the nanoparticle with an amphiphilic polymer, the amphiphilic polymer including at least one hydrophilic region and at least one hydrophobic region. The amphiphilic polymer can be dissolved in a water-miscible organic solvent to form a second process solution. The nanoparticles can be dissolved, suspended, or otherwise included in the second process solution. The second process solution can be continuously mixed with an aqueous solvent to form a second mixed solution from which a coated nanoparticle assembles and precipitates. The coated nanoparticle can include a core, a shell, and a coating. The coating can include an inner region and an outer region. The inner region can include the at least one hydrophobic region of the amphiphilic polymer. The outer region can include the at least one hydrophilic region of the amphiphilic polymer.

The amphiphilic polymer can be a random copolymer, a graft copolymer, a block copolymer, a diblock copolymer, a triblock copolymer, or a multiblock copolymer. For example, the amphiphilic polymer can be polystyrene-block-poly(ethylene glycol) (PS-b-PEG), poly(lactic acid)-block-poly(ethylene glycol) (PLA-b-PEG), poly(caprolactone)-block-poly(ethylene glycol) (PCL-b-PEG), poly (lactic-co-glycolic acid)-block-poly(ethylene glycol) (PLGA-b-PEG), poly(ethylene oxide)-block-poly(propylene oxide)-block-poly(ethylene oxide) (PEO-b-PPO-b-PEO), or poly(ethylene oxide)-block-poly(butylene oxide)-block-poly(ethylene oxide) (PEO-b-PBO-b-PEO).

The water-miscible organic solvent can include tetrahydrofuran (THF) and/or acetone and the aqueous solvent can be water.

In an embodiment of the invention, a nanoparticle can include a more polar region of a copolymer and a water soluble agent and a shell including a less polar region of the copolymer. The more polar region of the copolymer in the core can be crosslinked. The nanoparticle can also include a coating. The coating can include an inner region and an outer region. The inner region can include a hydrophobic region of an amphiphilic polymer. The outer region can include a hydrophilic region of the amphiphilic polymer.

DETAILED DESCRIPTION

Figure 1:
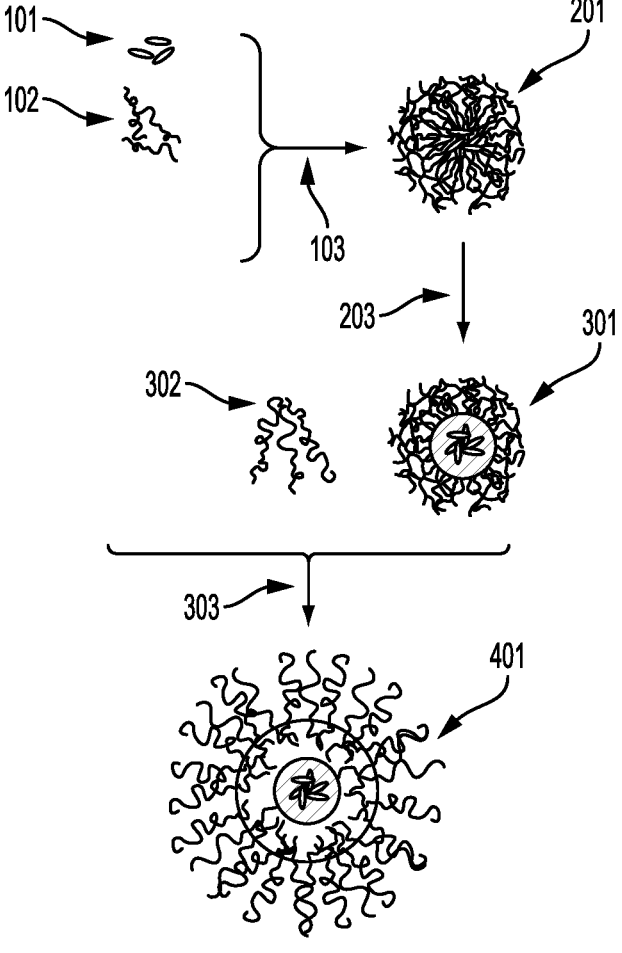
FIG. 1 illustrates steps in the production of nanoparticles according to the invention. An "inverse" nanoparticle can be formed of a copolymer that assembles into a nanoparticle having a hydrophilic core including a water soluble agent and a less polar shell 201. The core can be crosslinked to form an "inverse" nanoparticle with a crosslinked core 301. The "inverse" nanoparticle can be coated with an amphiphilic polymer to produce a structure that is stable in aqueous solution 401.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

Encapsulation and delivery of soluble therapeutics and biologics, including peptides, proteins, DNA, and RNA, is challenging. Biologics can exhibit poor stability, fast clearance times, immune recognition, and high costs. Nanoparticles, microparticles, and larger monoliths capable of releasing soluble therapeutics in a controlled manner that will protect them from degradation, clearance, and immune recognition are desired. Biologics are presently commonly delivered via injection, thus controlled release may reduce the frequency of drug administration and increase patient compliance.

It has been possible to make nanoparticles by rapid precipitation processes, described in U.S. Pat. No. 8,137,699

B2. However, these previous examples involved hydrophobic core materials that precipitated out of an aqueous phase upon mixing. It was unexpected that the process could be completely inverted and that a water soluble compound could be precipitated into a hydrophobic solution. It was unexpected that copolymers could be used in a reverse way in which the polar component is oriented inside the core of the particle and the hydrophobic less polar component is oriented into the less polar solution phase with stable particles resulting.

In this specification, the terms "nanoparticles", "particles", and "nanocarriers" are used interchangeably, unless a distinction is indicated by the context. Particles according to the invention that have hydrophilic or more polar cores are at times referred to as "inverse particles", to contrast them with particles that have hydrophobic or less polar cores. However, for the sake of brevity, when the context indicates that particles having hydrophilic or more polar cores according to the invention are being discussed, these may be simply referred to as "particles" or "nanoparticles".

The development of injectable polymeric depots for the prolonged release of biologics is a complex engineering challenge of optimizing biologic stability, encapsulation efficiency, loading, and release profile, as well as ease and scalability of production. That is, the delivery system for a biologic should protect, prolong the release of, reduce clearance times of, and reduce the frequency of administration of the biologic, as well as target the tissue(s) of interest. The aqueous processing conditions and lack of hydrophobic interfaces in hydrogel based delivery systems make them suitable for maintaining protein stability. However, the diffusion controlled release from these systems makes it difficult to produce degradable injectable gels capable of releasing biologics over periods of months or longer. Hydrophobic scaffolds are adept at more prolonged release, but the formulation methods can be too harsh for most large proteins. In the double emulsion method for forming nanocarriers, it is difficult to increase loading, encapsulation efficiency, protein stability, or optimize the release profile without negatively affecting another parameter. It is important to understand these failings in order to design new formulation methods. For example, newly investigated approaches of post-loading porous PLGA capitalize on fundamental research into the closure of pores on the microparticle surface during burst release as well as previous observations that protein desorption from the PLGA walls plays an important role in controlling the release rate. Ultimately, protein and peptide therapeutics cover a broad range of molecules, each with particular physical characteristics and processing needs; it is unlikely that a single polymeric depot will be suitable for the delivery of every biologic.

The delivery of agents such as protein and peptide therapeutics or other biologics from polymeric systems can be through release from a monolith (including erodible implantable devices), or release from micro or nanoparticles. Monoliths include erodible implantable devices. Micro and nanoparticles may be delivered systemically or in a local depot.

Release of therapeutics from polymeric systems may be controlled in one of two ways. In the first method, the therapeutic is conjugated to the polymeric material of the scaffold. The therapeutic is released when it is cleaved from the scaffold. This is most commonly done with hydrogels. Because conjugation entails the formation of new chemical bonds, the system is subject to more rigorous FDA approval and is thus generally undesirable. In the second method, the soluble therapeutics are encapsulated within an insoluble but erodible matrix. The erodible matrices are hydrophobic and must be processed with hydrophobic organic solvents. This method may be preferable because there is no chemical modification to the therapeutic.

Soluble materials can be encapsulated without chemical modification through either (1) mixing the material directly with a scaffold material (example: PLGA) in an organic solvent or (2) forming an emulsion. In method (1), the hydrophilic material often aggregates in the organic solvent. As the solvent is removed, even at low loadings, these aggregates produce percolating pathways resulting in an unfavorable burst release of encapsulated material. In order to improve the release profile, process (2) can be used. The soluble material is contained in an aqueous phase that is encapsulated in an outer, nonmiscible, organic solvent containing a hydrophobic scaffold material. Percolation is prevented and the emulsion is stabilized through the use of small molecule or polymeric surfactants. The emulsion process is completed in batches, which is not optimal for large scale production. Additionally, the high shear rates involved in the emulsification process may denature proteins and cleave DNA.

Flash NanoPrecipitation (FNP) is a previously patented process (U.S. Pat. No. 8,137,699 (herein, "'699 patent"), herein incorporated by reference in its entirety) to make nanoparticles with a hydrophobic core and hydrophilic stabilizing shell (Johnson, B. K., et al., AIChE Journal (2003) 49:2264-2282). This process allows for the high loading of hydrophobic material and can reproducibly produce particles ranging in size from the micelle size of the stabilizing material up to several hundred nanometers. Currently, the use of FNP has been limited to the encapsulation of core material with high log P values (hydrophobic). Flash NanoPrecipitation technology can encapsulating biologics with high encapsulation efficiency and loadings greater than 75 wt %.

In a method according to the invention, polymer protected core shell nanoparticles are made by rapid precipitation, so that the resulting particles contain hydrophilic material in their core, and an organic-solvent soluble (less hydrophilic) shell. These nanoparticles having a hydrophilic core and a less hydrophilic shell can be termed "inverse" nanoparticles, in contrast with the nanoparticles of the '699 patent having a hydrophobic core and a hydrophilic shell.

These "inverse" particles may be processed by covalently or non-covalent stabilizing the particles, adding a second coating of stabilizing material (layer by layer FNP), and/or by incorporating them into larger monoliths or microparticles.

Nanoparticle Formation

Flash NanoPrecipitation Process

The Flash NanoPrecipitation process can be used to create "inverse" particles with hydrophilic cores and/or with encapsulated water soluble agents, such as hydrophilic peptides. The process is illustrated in FIG. 1. A copolymer 102 can be dissolved in a polar process solvent at a concentration of at least 0.1% by weight, but preferably the concentration of copolymer is at least 0.2% by weight to form a first process solution. In an embodiment, the copolymer can be dissolved in the polar process solvent at a concentration in a range of from about 0.1 wt %, 0.2 wt %, 0.5 wt %, 1 wt %, 2 wt %, 5 wt %, 10 wt %, or 20 wt % to about 0.2 wt %, 0.5 wt %, 1 wt %, 2 wt %, 5 wt %, 10 wt %, 20 wt %, or 40 wt %. A person of skill in the art will appreciate that a factor such as the economics of a process can limit the constrain a lower bound of concentration, and that factors such as the viscosity of the process solution or the solubility limit of the copolymer in the polar process solvent can constrain an upper bound of concentration. For example, if the viscosity of the first process solution is much greater than that of the nonprocess solvent, mixing of the first process solution with the nonprocess solvent may be inhibited. A person of skill in the art will appreciate that factors such as the molecular weight of the copolymer and the composition of the copolymer can affect the maximum concentration that can be attained in the polymer solution before the viscosity becomes too high.

Examples of copolymers include but are not limited to block copolymers, graft copolymers, and random copolymers that contain regions with different solvent solubilities within the same copolymer. For example, a poly(n-butyl acrylate)-block-poly(acrylic acid) (PBA-b-PAA) diblock copolymer can be used. Examples of process solvents include, but are not limited to, water, alcohols, acetone, acetonitrile, dimethyl sulfoxide, dimethylformamide, and mixtures thereof. The process solvent can be heated or pressurized or both to facilitate dissolution of the copolymer, depending on the dissolution characteristics of the copolymer in the solvent.

Upon micromixing 103 the process solvent containing the copolymer with a less polar non-process solvent, the dissimilar solubility characteristics of regions or portions of the copolymer are manifested and the more polar portions of the copolymer can no longer exist in the soluble state, so that an "inverse" nanoparticle 201 precipitates.

In an embodiment, additive water soluble target molecules 101, for example, a hydrophilic peptide, can be added to the copolymer 102 in the process solvent. Upon creation of nanoparticles 201 with the copolymer, the additive target molecule 101 will be incorporated in the nanoparticle. Additive target molecules 101 that are poorly soluble in the non-process solvent are coated, encapsulated, or confined as a particulate core and sterically stabilized by the protective colloid of the copolymer 102. The nanoparticles maintain a small and stable size in the nonprocess solvent.

In another embodiment (not shown in FIG. 1), the target material and copolymer are dissolved in separate process solvent streams. The process solvent used to dissolve the copolymer and target material may be, but are not required to be, the same. These streams are simultaneously mixed with the non-process solvent. In another embodiment, the target material and copolymer are dissolved in a single process solvent stream. This stream is then rapidly mixed with a nonprocess solvent.

The intense micromixing 103 of the process solution and the non-process solvent can be effected in any number of geometries. The essential idea is that high velocity inlet streams cause turbulent flow and mixing that occurs in a central cavity. The time for process solvent/non-process solvent mixing is more rapid than the assembly time of the nanoparticles. While not meant to be limiting, two such geometries have been previously described and analyzed: the Confined Impinging Jet mixer (CIJ) (Johnson, B. K., Prud'homme, R. K. Chemical processing and micromixing in confined impinging jets. *AIChE Journal* 2003, 49, 2264-2282; Liu, Y., Fox, R. O. CFD predictions for chemical processing in a confined impinging-jets reactor. *AIChE Journal* 2006, 52, 731-744) or a multi-inlet vortex mixer (MIVM) (Liu, Y., Cheng, C., Liu, Y., Prud'homme, R. K., Fox, R. O. Mixing in a multi-inlet vortex mixer (MIVM) for flash nano-precipitation. *Chemical Engineering Science* 2008, 63, 2829-2842). These examples are meant to be illustrative rather than limiting or exhaustive.

The fast mixing and high energy dissipation involved in this process provide mixing timescales that are shorter than the timescale for nucleation and growth of particles, which leads to the formation of nanoparticles with active agent loading contents and size distributions not provided by other technologies. When forming the nanoparticles via Flash NanoPrecipitation, mixing occurs fast enough to allow high supersaturation levels, for example, as high as 10,000, of all components to be reached prior to the onset of aggregation. The supersaturation level is the ratio of the actual concentration of a material, for example, a copolymer, in a solvent to the saturation concentration of that material in that solvent. For example, the supersaturation levels can be at least greater than about 1, 3, 10, 30, 100, 300, 1000, or 3000 and can be at most about 3, 10, 30, 100, 300, 1000, 3000, or 10,000. The timescale of aggregation of the target material and copolymer self-assembly are balanced. Therefore, the target material and polymers precipitate simultaneously, and overcome the limitations of low active agent incorporations and aggregation found with the widely used techniques based on slow solvent exchange (e.g., dialysis). The Flash NanoPrecipitation process is insensitive to the chemical specificity of the components, making it a universal nanoparticle formation technique.

Figures 2A, 2B:
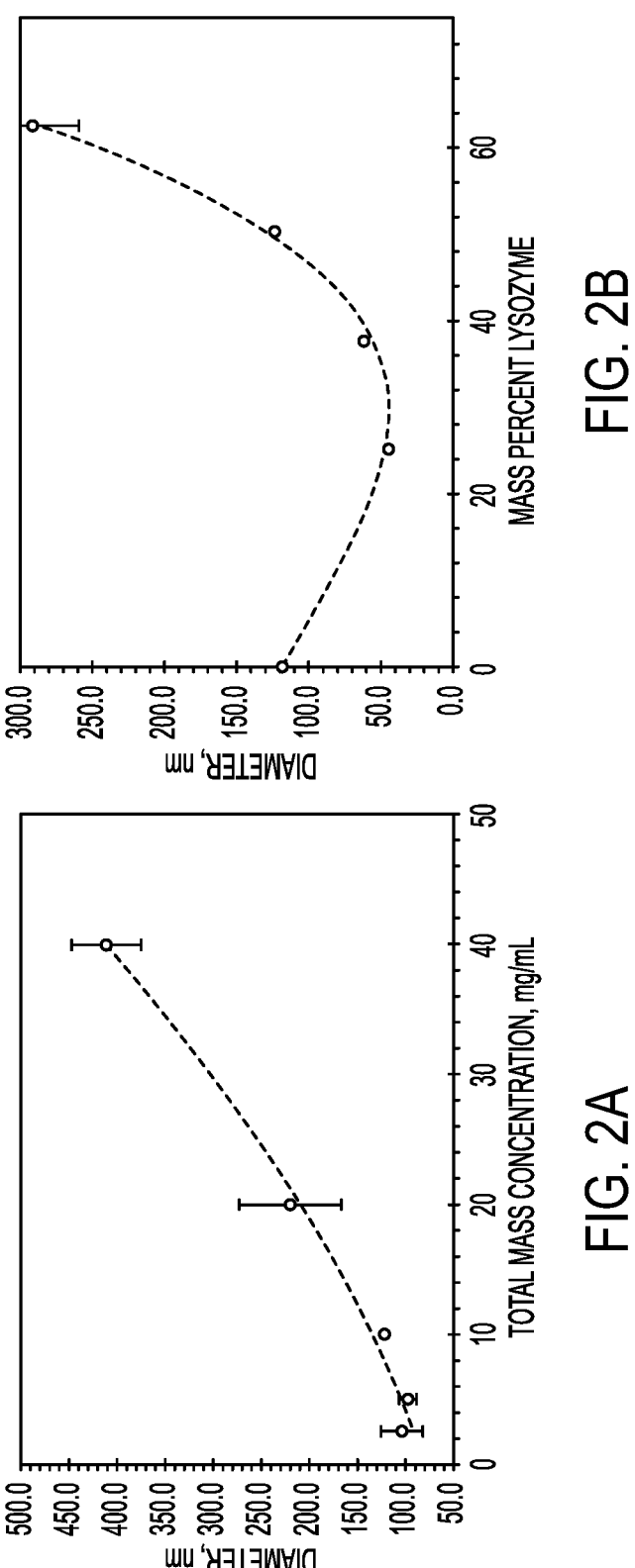
FIGS. 2A, 2B, 2C, and 2D illustrate how the variation of parameters in the Flash NanoPrecipitation process can control the diameter of the nanoparticles formed.
Figures 2C, 2D:
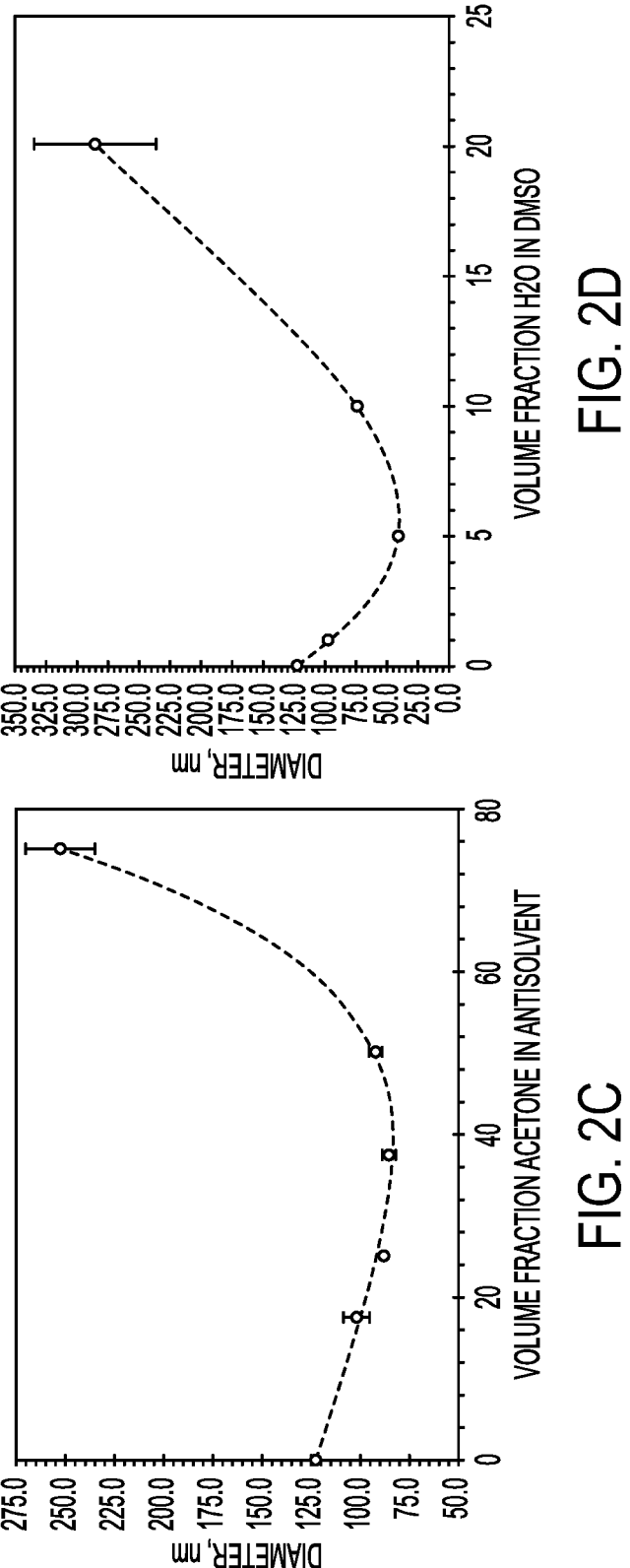

The size of the resulting nanoparticles from this process can be controlled by controlling the mixing velocity used to create them, the total mass concentration of the copolymer and target molecules in the process solvent, the process and non-process solvents, the ratio of the copolymer and target molecule, and the supersaturation of the target molecule and non-soluble portion of the copolymer upon mixing with the non-process solvent. That is, there are a number of "handles" that can be used to control the size of the nanoparticles. For example, in the formation of particles including lysozyme as the target molecule, the nanoparticle diameter can be varied with the total mass concentration as shown in FIG. 2A, with the mass percent of the target molecule lysozyme (mass percent of lysozyme with respect to lysozyme plus copolymer) as shown in FIG. 2B, with the volume fraction of acetone (fraction of acetone with respect to acetone plus chloroform) in the nonprocess solvent (antisolvent), the acetone being a poorer solvent for the hydrophilic lysozyme than the chloroform, as shown in FIG. 2C, and with the volume fraction of water ($H_2O$) in dimethylsulfoxide (DMSO) in the polar process solvent as shown in FIG. 2D. The experimental conditions under which this information was obtained is shown in Table 1, below.

TABLE 1

| Agent, Effect Studied, & FIG. | Process Stream | Nonprocess Stream | Bath |
|---|---|---|---|
| Lysozyme, Effect of loading on nanoparticle (NP) size, FIG. 2B | 500 uL DMSO, lysozyme and polymer at varying ratios, (lysozyme + polymer) = 10 mg/mL | 500 uL CHCl₃ | 4.5 mL CHCl₃ |
| Lysozyme, Nonprocess solvent effect, FIG. 2C | 500 uL DMSO, 5 mg/mL lysozyme, 5 mg/mL polymer | 500 uL antisolvent mixture | 4.5 mL antisolvent mixture |
| Lysozyme, Total mass concentration, FIG. 2A | 500 uL DMSO, equal masses of lysozyme and polymer | 500 uL CHCl₃ | 4.5 mL CHCl₃ |
| Lysozyme, Water effect, FIG. 2D | 500 uL DMSO with set vol % MQ, 5 mg/mL lysozyme, | 500 uL CHCl₃ | 4.5 mL CHCl₃ |

TABLE 1-continued

| Agent, Effect Studied, & FIG. | Process Stream | Nonprocess Stream | Bath |
|---|---|---|---|
| | 5 mg/mL polymer | | |

Without being bound by theory, for example, as the total mass concentration is increased (FIG. 2A), the protein aggregation rate can grow more quickly than the nucleation rate of polymer self assembly. At lower mass percentages of lysozyme, as the mass percentage of lysozyme is increased (FIG. 2B), the size initially decreases. Without being bound by theory, this may be because of a faster nucleation rate, i.e., with more nucleation sites there are more, but smaller, particles. Alternatively, this may be because of better packing of the PAA blocks, i.e., the negative charges of the PAA repel, and water and/or other core materials can shield this effect. At higher mass percentages of lysozyme, as the mass percentage of lysozyme is increased, the size increases. Without being bound by theory, this may be because at high percentages, large particles form because they have a higher volume to surface area ratio than small particles. As the volume fraction of acetone in the nonprocess solvent (anti-solvent) is increased (FIG. 2C), the nonprocess solvent becomes less polar. At lower acetone concentrations, as the acetone concentration is increased, the diameter of the particles formed decreases, because the nucleation rate of the copolymer increases and this dominates the size of the particles formed, i.e., with more nucleation sites more, but smaller, particles are formed. At higher acetone concentrations, as the acetone concentration is increased, the rate of aggregation of the lysozyme protein is enhanced and this dominates the size of the particles formed. As the volume fraction of water is increased (FIG. 2D), the process solvent becomes more polar. At lower water concentrations, as the water concentration is increased, the water acts as a nucleation site, helping the core of the nanoparticle to pack more tightly, so that the size of the nanoparticles decreases. At higher water concentrations, as the water concentration is increased, the water becomes integrated into the core, so that the size of the nanoparticles increases.

Nanoparticles as small as 40 nm diameter can be obtained at 50% loading (loading being the percentage of water soluble agent with respect to the water soluble agent plus copolymer). Stable nanoparticles can be obtained with 75% loading, although the diameter of the nanoparticles became too large to measure using dynamic light scattering (DSL).

Nanoparticles can be produced from copolymers that are dissolved in a process solvent with no target material added.

Using the methods according to the invention, particles can be made that have sizes in the range of 15 nm to 10500 nm, sizes in the range of 20 nm to 6000 nm, sizes in the range of 20 nm to 1000 nm, sizes in the range of 35 nm to 400 nm, or sizes in the range of 40 nm to 300 nm. Sizes can be determined by dynamic light scattering. For example, particles can be made that have sizes of at least about 15 nm, 20 nm, 35 nm, 40 nm, 50 nm, 100 nm, 200 nm, 300 nm, 400 nm, 600 nm, 1000 nm, 2000 nm, 4000 nm, or 6000 nm, and have sizes of at most about 20 nm, 35 nm, 40 nm, 50 nm, 100 nm, 200 nm, 300 nm, 400 nm, 600 nm, 1000 nm, 2000 nm, 4000 nm, 6000 nm, or 10500 nm. Sizes reported and cited herein are the intensity average reported values as determined by the Malvern Nanosizer deconvolution program. Other intensity weighted deconvolution methods can be used to determine sizes of the nanoparticles.

Encapsulated Material

Encapsulated material (target molecules) must be sufficiently polar that it rapidly precipitates in the less polar non-process solvent. Molecules that do not meet these criteria may be chemically modified to increase their water solubility and propensity to precipitate in the organic non-process solvent. Examples of biologic material that may be encapsulated include, but are not limited to, peptides, proteins, DNA, RNA, saccharides, and derivatives, conjugates, and/or analogs thereof. For example, glucagon-like peptide-1 (GLP-1) may be encapsulated. Small molecule water soluble therapeutics and imaging agents may also be encapsulated. Soluble stabilizing agents may be encapsulated in particles to provide stability to the particle for its use or for subsequent processing steps. Any of these materials may also be co-precipitated within a single particle. Hydrophilic material may be encapsulated for the sole purpose of adding stability to the particles during post processing. For example, material with molecular weights between 100 and 10,000,000 Daltons (Da) may be encapsulated. Material with molecular weights between 250 and 10,000,000 Da may be encapsulated. Material with molecular weights between 100 and 1,000,000 Da may be encapsulated. Material with molecular weights between 250 and 1,000,000 Da may be encapsulated. Material with molecular weights between 100 and 200,000 Da may be encapsulated.

Certain encapsulated materials may be multifunctional. For example, tobramycin is cationic and can itself be cross-linked with a copolymer.

The encapsulated material may be incorporated into the particle at a range of loadings. For example, the mass of the encapsulated material may be greater than or equal to the mass of the copolymer. For example, the concentration of the encapsulated material in the first process solution may be from about 0.1 wt %, 0.2 wt %, 0.5 wt %, 1 wt %, 2 wt %, 5 wt %, 10 wt %, or 20 wt % to about 0.2 wt %, 0.5 wt %, 1 wt %, 2 wt %, 5 wt %, 10 wt %, 20 wt %, or 40 wt %.

Solvents

Formation of nanoparticles requires a process solvent and non-process solvent stream. The process and non-process solvents may be a pure (that is, a single) liquid compound or a mixture of two or more pure liquid compounds. Other non-liquid compounds that aid in the solvent quality of the streams may be added and are also considered part of the solvent. These excipient compounds may or may not be in the final nanoparticle or microparticle construct, depending on the requirements of the final product.

The polar process solvent containing the copolymer is chosen such that the copolymer is molecularly dissolved. This requires that the process solvent solubilize all parts of the copolymer. The process solvent containing the material to be encapsulated, if present, is also chosen such that material is molecularly dissolved. These process solvents may be, but are not required to be, the same. In some cases, both the copolymer and material to be encapsulated may be dissolved in a single solution of the process solvent. In order to dissolve the water soluble material to be encapsulated, the process solvent is more polar than the non-process solvent. Examples of process solvents include, but are not limited to, water, alcohols, methanol, ethanol, dimethyl formamide (DMF), dimethyl sulfoxide (DMSO), acetonitrile, acetone, N-methyl pyrrolidone (NMP), and mixtures thereof. Acids, bases, and salts are a few examples of additives that may be used to aid in the solubilization of the copolymer and encapsulated material in the process solvent.

The solutions of process solvent containing copolymer and material to be encapsulated are mixed with a nonprocess solvent. The non-process solvent must be capable of changing the local molecular environment of the copolymer and causing local precipitation of the more polar sections of the polymer. The nonprocess solvent is chosen such that the more polar sections of the copolymer rapidly precipitate and the more nonpolar (less polar) sections of the copolymer remain solubilized. Thus, the copolymer will self-assemble into micelles or other structures in the nonprocess solvent. The nonprocess solvent is chosen such that the target material to be encapsulated rapidly precipitates in the final mixture. In most cases it is preferable for the process and non-process solvents to be fully miscible at the final composition. In some cases, no more than 20 volume percent of the process solvent may phase separate in the final composition. In general, this is only acceptable if the phase separated solvent goes to the core of the particles and there is no macroscopic separation. Nonprocess solvents include, but are not limited to, chloroform, dichloromethane, alkanes such as hexane, ethers such as diethyl ether, tetrahydrofuran (THF), toluene, acetone, and mixtures thereof. Acids, bases, and salts are a few examples of additives that may be used to aid in the precipitation of the encapsulated material and sections of the copolymer. Solvent choices are made based on the solubilities of the copolymer and encapsulated materials. It is important to note that process solvents of one system may work well as the nonprocess solvent in another system, thus the examples given above for process and nonprocess solvents should not be considered distinct.

Copolymers

The stabilizing polymer can be a copolymer of a more polar block coupled with a more nonpolar (less polar) block. The term "block" may be interpreted as either a distinct domain with a single molecular composition, or it may mean a region of the polymer chain which has regions that are predominantly more polar and other regions that are less polar. The polarity may be imparted by the monomers comprising the polymer backbone or grafted pendant groups or chains attached to the main polymer backbone. For example, the copolymer may be amphiphilic (the more nonpolar block is not water soluble), however, this is not a requirement and copolymers may be fully water soluble or fully non-water soluble, as long as solubilities of the blocks differ significantly enough in the nonprocess solvent. The copolymer should self-assemble in the nonprocess solvent, with the more polar blocks precipitating and the more nonpolar blocks remaining soluble. When used in the FNP process to make particles, the more polar blocks go to the core of the particle, and the more nonpolar blocks form a sterically protective shell. The sterically protective shell prevents particle aggregation and prevents percolation of encapsulated material during post processing steps.

Nanoparticles formed by the disclosed process can be formed with graft, block, or random copolymers. For example, these copolymers can have a molecular weight between about 1000 g/mole and about 1,000,000 g/mole, or between about 3000 g/mole and about 25,000 g/mole, or at least about 2000 g/mole.

The copolymers are comprised of repeat units or blocks that have different solubility characteristics. Typically, these repeat units are in groups of at least two comprising a block of a given character. Depending on the method of synthesis, these blocks could be of all the same repeat unit or contain different repeat units dispersed throughout the block, but still yielding blocks of the copolymer with polar and more non-polar portions. These blocks can be arranged into a series of two blocks (diblock) or three block (triblock), or more (multiblock), forming the backbone of a block copolymer. In addition, the polymer chain can have chemical moieties covalently attached or grafted to the backbone. Such polymers are graft polymers. Block units making up the copolymer can occur in regular intervals or they can occur randomly making a random copolymer. In addition, grafted side chains can occur at regular intervals along the polymer backbone or randomly making a randomly grafted copolymer. In graft polymers, polar blocks may be grafted on a non-polar polymer. More commonly, non-polar blocks are grafted on a more polar polymer chain. In graft copolymers, the length of a grafted moiety can vary. Preferably, the grafted segments are equivalent to 2 to 22 ethylene units in length. In addition, the grafting of the polymer backbone can be useful to enhance solvation or nanoparticle stabilization properties.

The copolymer used in the compositions and methods of the invention may be comprised of blocks of at least two repeat units or with a minimum contour length the equivalent of at least 25 ethylene units. Contour lengths are the linear sum of the polymer backbone, the molecular dimensions of which can be approximated using the Polymer Handbook, 4th Edition, eds. J. Brandrup, E. H. Immergut, and E. A. Grulke, assoc. ed. A. Abe, D. R. Bloch, 1999, New York, John Wiley & Sons, which is hereby incorporated by reference in its entirety.

Examples of suitable nonpolar blocks in a copolymer include but are not limited to the following: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, vinyl phenols and vinyllimidazole; aminoalkyls including aminoalkylacrylates, aminoalkylsmethacrylates, and aminoalkyl(meth)acrylamides; styrenes; cellulose acetate phthalate, cellulose acetate succinate, hydroxypropylmethylcellulose phthalate, poly(D,L-lactide), poly(D,L-lactide-co-glycolide), poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), lactic acid, caprolactone, glycolic acid, and their copolymers (see generally, Illum, L., Davids, S. S. (eds.) Polymers in Controlled Drug Delivery Wright, Bristol, 1987; Arshady, J. Controlled Release 17:1-22, 1991; Pitt, Int. J. Phar. 59:173-196, 1990; Holland et al., J. Controlled Release 4:155-0180, 1986); hydrophobic peptide-based polymers and copolymers based on poly(L-amino acids) (Lavasanifar, A., et al., Advanced Drug Delivery Reviews (2002) 54:169-190), poly(ethylene-vinyl acetate) ("EVA") copolymers, silicone rubber, polyethylene, polypropylene, polydienes (polybutadiene, polyisoprene and hydrogenated forms of these polymers), maleic anhydride copolymers of vinyl methylether and other vinyl ethers, polyamides (nylon 6,6), polyurethane, poly(ester urethanes), poly(ether urethanes), poly(esterurea). For example, polymeric blocks can include poly(ethylenevinyl acetate), poly(D,L-lactic acid) oligomers and polymers, poly(L-lactic acid) oligomers and polymers, poly(glycolic acid), copolymers of lactic acid and glycolic acid, poly(caprolactone), poly(valerolactone), polyanhydrides, copolymers of poly(caprolactone) or poly(lactic acid) For non-biologically related applications polymeric blocks can include, for example, polystyrene, polyacrylates, and butadienes.

Natural products with sufficient hydrophobicity to act as the non-polar portion of the polymer include: hydrophobic vitamins (for example vitamin E, vitamin K, and A), carotenoids, and retinols (for example, beta carotene, astaxanthin, trans and cis retinal, retinoic acid, folic acid, dihydrofolate, retinylacetate, retinyl palmintate), cholecalciferol, calcitriol, hydroxycholecalciferol, ergocalciferol, alpha-tocopherol, alpha-tocopherol acetate, alphatocopherol nicotinate, and estradiol. For example, a natural product is vitamin E which can be readily obtained as a vitamin E succinate, which facilitates functionalization to amines and hydroxyls on the active species.

Examples of suitable polar blocks in an amphiphilic polymer that is a block copolymer include, but are not limited to the following: carboxylic acids including acrylic acid, methacrylic acid, itaconic acid, and maleic acid; polyoxyethylenes or poly ethylene oxide; polyacrylamides and copolymers thereof with dimethylaminoethylmethacrylate, diallyldimethylammonium chloride, vinylbenzylthrimethyl-ammonium chloride, acrylic acid, methacrylic acid, 2-crry-lamideo-2-methylpropane sulfonic acid and styrene sulfonate, polyvincyl pyrrolidone, starches and starch derivatives, dextran and dextran derivatives; polypeptides, such as polylysines, polyarginines, polyaspartic acids, polyglutamic acids; poly hyaluronic acids, alginic acids, polylactides, polyethyleneimines, polyionenes, polyacrylic acids, and polyiminocarboxylates, gelatin, and unsaturated ethylenic mono or dicarboxylic acids. To prepare anionic copolymers, acrylic acid, methacrylic acid, and/or poly aspartic acid polymers can be used. To produce cationic copolymers, DMAEMA (dimethylaminoethylmethacrylate), polyvinyl pyridine (PVP), and/or dimethylaminoethylacrylamide (DMAMAM) can be used. A listing of suitable polar, water soluble, polymers can be found in Handbook of Water-Soluble Gums and Resins, R. Davidson, McGraw-Hill (1980).

The lists above of nonpolar and polar polymers should not be considered exclusive of one another. Copolymers of two polymers given in a single list may have sufficient differences in solubilities in a given nonprocess solvent to be used in this process. As an illustrative example, poly(ethylene oxide) and poly(acrylic acid) are both given in the list of polar polymers. However, poly(ethylene oxide) is soluble in chloroform and acetone, while poly(acrylic acid) is not. Therefore, copolymers of poly(ethylene oxide) and poly(acrylic acid) may be used in this process with chloroform or acetone as the nonprocess solvent.

Nanoparticle Processing

Particle Stabilization

The particles are formed and stable in the organic nonprocess solvent. In most applications, it is required that the final construct be stable in aqueous environments for a set, nonnegligible amount of time. In order to process the particles into an aqueous environment, particle stabilization is required. Without stabilization, the particle may dissolve, aggregate, and/or release the water soluble target material from the core.

In an embodiment according to the invention, sections of the core of the particle may be stabilized The core refers to the more polar sections of the copolymer and encapsulated material. Material may be incorporated into the core specifically for the purpose of particle stabilization. For example, the portions of the copolymer in the core may be crosslinked 203 to form a particle with a crosslinked core 301. In another embodiment, the shell of the particle may be stabilized. The shell refers to the more nonpolar sections of the copolymer that are soluble in the nonprocess solvent.

Stabilization can involve the formation of new covalent bonds. For example, the copolymer of the core (and, in some cases, the encapsulated material) of the particle may be cross-linked through the formation of new covalent bonds. The bonds may be formed directly between groups on the copolymer. Covalent bonds may be formed by adding a crosslinking material to the core for the specific purpose of cross-linking the polymer in the core. The crosslinking material (stabilizing material) may be added to the core of the particle during the FNP process. For example, the crosslinking material can be included in the process solvent. As another example, the crosslinking material can be included in the nonprocess solvent.

Alternatively, the crosslinking material may be added to the solution after the particle has formed. For example, the particle may be "incubated" with a crosslinking material, such as a metal salt, and the crosslinking material may interact with a more polar portion of the copolymer, e.g., PAA, for example, through ionic and/or chelation effects. The degree of crosslinking realized can then be characterized by suspending the particle in a good solvent for the more polar portion of the copolymer. Particles with tight (dense) crosslinking can exhibit minimal swelling and can be associated with high levels of metal partitioning into the hydrophilic core and strong metal interactions with the more polar part of the polymer. Particles with loose crosslinking can exhibit high levels of swelling and can be associated with low levels of metal partitioning into the hydrophilic core and weak metal interactions with the more polar part of the polymer. If the partitioning of the metal into the core is very low and or the interaction of the metal with the more polar part of the polymer is very weak, then the particle may disassemble and dissolve in the solvent.

If the crosslinking material is added after the particles have been formed, the crosslinking may be diffusion limited and only occur on the outer layers of the core. If the crosslinking material is added to the solution after the particles have been formed, the particle may be cross-linked throughout the core if the core is swollen with solvent or if the cross-linking material is small enough to diffuse throughout the core. The shell of the particle may be cross-linked through the formation of new covalent bonds. The bonds may be formed directly between groups on the copolymer, or through the addition of an extra crosslinking material.

Examples of covalent chemistries that may be used include, but are not limited to carbodiimide coupling of carboxylic acids to alcohols or carboxylic acids to amines, the coupling of activated esters to alcohols or amines, maleimide-thiol chemistry, Micheal addition, azidealkyne "click" chemistry, UV or light activated chemistries, and/or disulfide formation.

Stabilization can be obtained through non-covalent interactions. The core of the particle may be cross-linked through non-covalent interactions. The interactions may be directly between groups on the copolymer. Non-covalent interactions may be formed by adding a crosslinking material to the core for the specific purpose of cross-linking the polymer in the core. This crosslinking material may be added to the core of the particle during the FNP process. Alternatively, this crosslinking material may be added to the solution after the particle has formed. If the crosslinking material is added after the particles have been formed, the crosslinking may be diffusion limited and only occur on the outer layers of the core. If the crosslinking material is added to the solution after the particles have been formed, the particle may be crosslinked throughout the core if the core is swollen with solvent or if the crosslinking material is small enough to diffuse throughout the core. The shell of the particle may be cross-linked through noncovalent interactions. The interactions may be formed directly between groups on the copolymer, or through the addition of an extra crosslinking material.

Examples of non-covalent interactions that may be used include, but are not limited to, ionic interactions, acid-base interactions, metal chelation, interactions between polyhistidines and a metal such as nickel, and/or strong hydrogen bonding. An example of non-covalent particle stabilization is the use of Cr(III) to stabilize the poly(acrylic acid) core of a nanoparticle. For example, chromium (III) acetate and/or chromium (III) bromide can be used as crosslinking materials. The crosslinking may proceed through ligand exchange. The solvents used can act as ligands. For example, the interaction of the cation in a crosslinking salt should be stronger with the more polar portion of the copolymer to be crosslinked in the core than with the anion in the salt.

Other crosslinking materials (crosslinking agents) that can be used to induce non-covalent crosslinking include alkaline earth halides, magnesium halides, calcium halides, metal halides, transition metal halides, and iron halides. Metal salts can be used. Additional crosslinking materials that can be used are metal acetates, alkaline earth acetates, transition metal acetates, and calcium acetate. The crosslinking ability of a given cation (e.g., a metal) depends on the accompanying anion. The crosslinking ability of a crosslinking material, e.g., a salt, can depend on the process solvent and nonprocess solvent used. A crosslinking material can include a metal that is biological interesting or functional or otherwise useful. For example, Fe(III), Ca(II), and Zn(II) cations are biocompatible. Gd(III) (gadolinium(III)) is active in magnetic resonance imaging (MRI), and, therefore, can be useful as a tracer.

Some crosslinking materials that work well when conducting crosslinking during nanoparticle formation, e.g., during the FNP process, include polyamines, such as spermine, and certain chloride salts, such as magnesium chloride, calcium chloride, and iron(III) chloride. For example, such crosslinking materials can be used with PBA-b-PAA copolymer, methanol, dimethylsulfoxide, and/or water as the process solvent, and acetone and/or chloroform as the nonprocess solvent. It may be necessary to include some water in the process solvent for the crosslinking to occur. In some systems, calcium chloride, magnesium chloride, and spermine may act as weak crosslinkers. An iron(III) salt, such as iron(III) chloride, may induce strong crosslinking.

Multiple types of stabilization chemistries may be employed within a given particle. Stabilization may occur in the core, in the shell, at the interface, or in multiple locations within a given particle.

For many applications, particle degradation and release of encapsulated material is required. The type of stabilization chemistry used, and the density of the crosslinked network, may affect the degradation kinetics of the particle. The type of stabilization chemistry used, and the density of the cross-linked network, may also or alternatively affect the release kinetics of encapsulated material from the core of the particle.

For some applications, it is required that the encapsulated material is not chemically modified. In these cases, non-covalent interactions should be used to stabilize the particle. However, covalent crosslinking may be used as long as the chemistry is specific to the copolymer and does not modify the encapsulated material.

After crosslinking, if the more nonpolar blocks of the copolymer are water soluble, the particles may be placed directly in an aqueous environment. The particle shell will provide steric stabilization. An example is particles composed of poly(acrylic acid)-b-poly(ethylene oxide) that are formed with chloroform as the non-process solvent and use Cr(III) to crosslink the poly(acrylic acid) core. Once the particles have been crosslinked they may be placed in an aqueous environment, and the poly(ethylene oxide) will provide steric stabilization and prevent particle aggregation.

After crosslinking, if the more non-polar blocks of the copolymer are short and the core of the particle is charged, the particles may be placed in an aqueous environment. This requires that the core swell sufficiently in the aqueous environment such that charged patches of the core are no longer protected by the nonpolar blocks of the copolymer. These patches must be sufficiently large and charged in order for the particles to not aggregate (charge stabilized).

Particle Coating—Layer by Layer Flash NanoPrecipitation

After particle stabilization, a second layer of an amphiphilic polymer 302 may be coated onto 303 the surface of the particle 301 to form a nanoparticle having a coating 401 (see FIG. 1). This second layer of amphiphilic polymer 302 can be referred to as the "coating". This coating may be done to modify the surface properties of the particle to make it stable in an aqueous environment. For example, this may be useful if the shell of the particle—that is, the more nonpolar sections of the copolymer—is not water soluble. Particle coating with a stabilizing amphiphilic polymer 302 may be accomplished through a second Flash NanoPrecipitation step 303. The particles 301 must be sufficiently stabilized prior to being coated to be able to withstand the coating process.

The stabilizing amphiphilic polymer 302 can be a copolymer of a hydrophilic block coupled with a hydrophobic block. Nanoparticles coated by the disclosed process can be coated with graft, block, or random amphiphilic copolymers. These amphiphilic polymers can have a molecular weight of between about 1000 g/mole and about 50,000 g/mole, between about 3000 g/mole and about 25,000 g/mole, or at least 2000 g/mole. Examples of suitable hydrophobic blocks in an amphiphilic polymer that is a block copolymer include, but are not limited to the following: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, vinyl phenols and vinyllimidazole; aminoalkyls including aminoalkylacrylates, aminoalkylmethacrylates, and aminoalkyl(meth)acrylamides; styrenes; cellulose acetate phthalate, cellulose acetate succinate, hydroxypropylmethylcellulose phthalate, poly(D,L lactide), poly(D,L-lactide-co-glycolide), poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers (see generally, Illum, L., Davids, S. S. (eds.) Polymers in Controlled Drug Delivery Wright, Bristol, 1987; Arshady, J. Controlled Release 17:1-22, 1991; Pitt, Int. J. Phar. 59:173-196, 1990; Holland et al., J. Controlled Release 4:155-0180, 1986); hydrophobic peptide-based polymers and copolymers based on poly(L-amino acids) (Lavasanifar, A., et al., Advanced Drug Delivery Reviews (2002) 54:169-190), poly(ethylene-vinyl acetate)

("EVA") copolymers, silicone rubber, polyethylene, polypropylene, polydienes (polybutadiene, polyisoprene, and hydrogenated forms of these polymers), maleic anhydride copolymers of vinyl methylether and other vinyl ethers, polyamides (nylon 6,6), polyurethane, poly(ester urethanes), poly(ether urethanes), and poly(esterurea). For example, polymeric blocks include poly(ethylenevinyl acetate), poly (D,L-lactic acid) oligomers and polymers, poly(L-lactic acid) oligomers and polymers, poly(glycolic acid), copolymers of lactic acid and glycolic acid, poly(caprolactone), poly(valerolactone), polyanhydrides, copolymers of poly (caprolactone) or poly(lactic acid). For example, for non-biologically related applications polymeric blocks can include polystyrene, polyacrylates, and butadienes.

Natural products with sufficient hydrophobicity to act as the hydrophobic portion of the amphiphilic polymer include, for example, hydrophobic vitamins (for example, vitamin E, vitamin K, and vitamin A), carotenoids and retinols (for example beta carotene, astaxanthin, trans and cis retinal, retinoic acid, folic acid, dihydrofolate, retinylacetate, retinyl palmitate), cholecalciferol, calcitriol, hydroxycholecalciferol, ergocalciferol, alpha-tocopherol, alpha-tocopherol acetate, alpha-tocopherol nicotinate, and estradiol. The preferred natural product is vitamin E which can be readily obtained as a vitamin E succinate, which facilitates functionalization to amines and hydroxyls on the active species.

Examples of suitable hydrophilic blocks in an amphiphilic polymer include but are not limited to the following: carboxylic acids including acrylic acid, methacrylic acid, itaconic acid, and maleic acid; polyoxyethylenes or poly ethylene oxide; polyacrylamides and copolymers thereof with dimethylaminoethylmethacrylate, diallyldimethylammonium chloride, vinylbenzylthrimethylammonium chloride, acrylic acid, methacrylic acid, 2-crrylamideo-2-methylpropane sulfonic acid and styrene sulfonate, polyvincyl pyrrolidone, starches and starch derivatives, dextran and dextran derivatives; polypeptides, such as polylysines, polyarginines, polyglutamic acids; poly hyaluronic acids, alginic acids, polylactides, polyethyleneimines, polyionenes, polyacrylic acids, and polyiminocarboxylates, poly(ethylene glycol), gelatin, and unsaturated ethylenic mono or dicarboxylic acids. For example, the hydrophilic blocks can be of poly(ethylene glycol). For example, the hydrophilic blocks can be of poly(ethylene oxide) and poly hydroxyl propyl acrylamide and methacrylamide to prepare neutral blocks since these materials are in currently approved medical applications. To prepare anionic copolymers acrylic acid and methacrylic acid and poly aspartic acid polymers can be used. To produce cationic amphiphilic polymers DMAEMA (dimethylaminoethylmethacrylate), polyvinyl pyridine (PVP) or dimethylaminoethylacrylamide (DMAMAM) can be used.

For example, the blocks can be diblock, triblock, or multiblock repeats. Preferably, block copolymers can include blocks of polystyrene, polyethylene, polybutyl acrylate, polybutyl methacrylate, polylactic acid (PLA), polyglutamic acid (PGA) and PLGA copolymers, polycaprolactone, polyacrylic acid, polyoxyethylene and polyacrylamide. A listing of suitable hydrophilic polymers can be found in Handbook of Water-Soluble Gums and Resins, R. Davidson, McGraw-Hill (1980).

For example, the amphiphilic polymer can be polystyrene-block-poly(ethylene glycol) (PS-b-PEG), poly(lactic acid)-block-poly(ethylene glycol) (PLA-b-PEG), poly (caprolactone)-block-poly(ethylene glycol) (PCL-b-PEG), poly(lactic-co-glycolic acid)-block-poly(ethylene glycol) (PLGA-b-PEG), or tri-block forms of the diblock copolymers listed above. Furthermore, triblock copolymers such as poly(ethylene oxide)-block-poly(propylene oxide)-block-poly(ethylene oxide) (PEO-b-PPO-b-PEO) or poly(ethylene oxide)-block-poly(butylene oxide)-block-poly(ethylene oxide) (PEO-b-PBO-b-PEO) may be used.

In an amphiphilic polymer that is a graft copolymer, the length of a grafted moiety can vary. For example, the grafted segments can be alkyl chains of 4 to 22 carbons or equivalent to 2 to 11 ethylene units in length. Grafted groups may also include lipids, phospholipids or cholersterol. The grafting of the polymer backbone can be useful to enhance solvation or nanoparticle stabilization properties. A grafted butyl group on the hydrophobic backbone of a diblock copolymer of a polyethylene and polyethylene glycol should increase the solubility of the polyethylene block. Suitable chemical moieties grafted to the block unit of the copolymer comprise alkyl chains containing species such as amides, imides, phenyl, carboxy, aldehyde, or alcohol groups.

The method of coating the nanoparticles is as previously described by Johnson et al., termed "Flash NanoPrecipitation" (FNP), Johnson, B. K., et al., AIChE Journal (2003) 49:2264-2282 and U.S. Pat. No. 8,137,699, which are incorporated herein by reference in their entirety. FNP is a rapid, single-step block copolymer-directed precipitation process. The particles can be treated to remove residual solvent, such as chloroform. The particles and amphiphilic block copolymers are dissolved in a water-miscible organic solvent. Acceptable solvents include, but are not limited to, tetrahydrofuran (THF), dimethylformamide, acetonitrile, acetone, low molecular weight alcohols such as methanol and ethanol, dimethyl sulfoxide (DMSO), or mixtures thereof. Solvent quality is rapidly reduced by micromixing against water or an aqueous buffer or mixture to produce supersaturation levels as high as 10,000 to drive rapid precipitation wherein the time of mixing is faster than the aggregation of the nanoparticles and balances with the timescale of block copolymer self-assembly. This process is capable of producing controlled size, polymer stabilized, and protected nanoparticles.

The Flash NanoPrecipitation coating technique is based on amphiphilic diblock copolymer arrested aggregation of the nanoparticles produced by the initial FNP process. Amphiphilic diblock copolymers dissolved in a good solvent can form micelles when the solvent quality for one block is decreased. The intense micromixing can be effected in any number of geometries. The essential idea is that high velocity inlet streams cause turbulent flow and mixing that occurs in a central cavity. The time for solvent/antisolvent mixing is more rapid than the assembly time of the nanoparticles. While not meant to be limiting, two such geometries have been previously described and analyzed: the Confined Impinging Jet mixer (CIJ) or a multi-inlet vortex mixer (MIVM). These examples are meant to be illustrative rather than limiting or exhaustive, and were discussed previously.

The vortex mixer consists of a confined volume chamber where one jet stream containing the diblock copolymer dissolved and particles suspended in a water-miscible solvent, such as THF, acetone, or a mixture, is mixed at high velocity with another jet stream containing water, an antisolvent for the nanoparticle shell and the hydrophobic block of the copolymer. The fast mixing and high energy dissipation involved in this process provide timescales that are shorter than the timescale for nucleation and growth of particles, which leads to the formation of nanoparticles with active agent loading contents and size distributions not provided by other technologies. When coating the nanoparticles via Flash NanoPrecipitation, mixing occurs fast enough to allow high supersaturation levels of all components to be reached prior to the onset of aggregation. Therefore, the particles and polymers precipitate simultaneously, and overcome the limitations of low active agent incorporations and aggregation found with the widely used techniques based on slow solvent exchange (e.g., dialysis). The Flash NanoPrecipitation process is insensitive to the chemical specificity of the components, making it a universal nanoparticle coating technique.

The coating formed by the amphiphilic polymer can have an inner region and an outer region. The inner region can include hydrophobic regions of the amphiphilic copolymer, and the outer region can include hydrophilic regions of the amphiphilic copolymer.

The concentrations, amphiphilic polymers, and solvents used in the coating process may be optimized such that individual particles are coated, or particles aggregate to a desired size prior to being coated. For example, increasing the amount of amphiphilic polymer used to coat concentrated nanoparticles relative to the amount of copolymer in the particles themselves can result in smaller particle diameter. When coating concentrated nanoparticles, more than one nanoparticle can be incorporated in a stabilizing shell of amphiphilic polymer.

When coating dilute nanoparticles, the amount of amphiphilic polymer relative to the amount of copolymer in the particles themselves may have little or no effect on the resultant particle diameter.

Coating the particles modifies the surface chemistry of the particles. Coating the particles may change the stability and degradation kinetics of the particles in an aqueous media. Coating the particles may change the release kinetics of encapsulated material.

Coated nanoparticles have been formed with glutathione (GSH), lysozyme, vancomycin, or tobramycin as the encapsulated material.

Particle Incorporation into Microparticles and Monoliths

The particles may be incorporated into microparticles or larger monoliths. The hydrophobic polymer block can prevent percolation and allow for high loading of the encapsulated material, stabilization during processing, and controlled release.

If the particles are being incorporated into a hydrophobic scaffold that is processed in a poor solvent for the particle core, the particle may be adequately stabilized by the less polar polymer block prior to processing.

The hydrophilic active compound or biologic compound is captured in the interior of the particle formed by the first processing step into the hydrophobic process solvent. Organic polymers soluble in the hydrophobic process solvent may be added to the particle dispersion. Polymers that might be added include biocompatible and or biodegradable polymers. Nonlimiting examples of these polymers would include: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate and copolymers of these acrylates; acrylonitriles; methacrylonitrile; vinyls including vinyl acetate, vinylversatate, vinylpropionate, vinylformamide, vinylacetamide, vinylpyridines, vinyl phenols and vinyllimidazole; aminoalkyls including aminoalkylacrylates, aminoalkylsmethacrylates, and aminoalkyl(meth)acrylamides; styrenes; cellulose acetate phthalate, cellulose acetate succinate, hydroxypropylmethylcellulose phthalate, poly(D,L lactide), poly(D,L-lactide-co-glycolide), poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers (see generally, Illum, L., Davids, S. S. (eds.) Polymers in Controlled Drug Delivery Wright, Bristol, 1987; Arshady, J. Controlled Release 17:1-22, 1991; Pitt, Int. J. Phar. 59:173-196, 1990; Holland et al., J. Controlled Release 4:155-0180, 1986); hydrophobic peptide-based polymers and copolymers based on poly(L-amino acids) (Lavasanifar, A., et al., Advanced Drug Delivery Reviews (2002) 54:169-190), poly(ethylene-vinyl acetate) ("EVA") copolymers, silicone rubber, polyethylene, polypropylene, polydienes (polybutadiene, polyisoprene and hydrogenated forms of these polymers), maleic anyhydride copolymers of vinyl methylether and other vinyl ethers, polyamides (nylon 6,6), polyurethane, poly(ester urethanes), poly(ether urethanes), poly(esterurea). Examples of polymeric blocks include poly(ethylenevinyl acetate), poly(D,L-lactic acid) oligomers and polymers, poly(L-lactic acid) oligomers and polymers, poly(glycolic acid), copolymers of lactic acid and glycolic acid, poly(caprolactone), poly(valerolactone), polyanhydrides, copolymers of poly(caprolactone) or poly(lactic acid) For non-biologically related applications particularly preferred polymeric blocks include polystyrene, polyacrylates, and butadienes.

After addition of these polymers or mixtures thereof, the resulting dispersed biologic particles in the polymer containing hydrophobic organic solution phase can be formed into the desired microparticle or monolith by techniques well known in the field. These include emulsion-stripping techniques as described by Domb (U.S. Pat. No. 5,578,325) or Gibson (U.S. Pat. No. 6,291,013 B1), spray drying, or molding to form a solid matrix containing the encapsulated hydrophilic active, such as a biologic. The matrix can be dried by spray drying, by pan drying, or by molding processes to obtain a solid final matrix containing the encapsulated active or biologic. Release is then effected by dissolution, erosion, or swelling of the matrix phase. This encapsulation followed by matrix formation enables much higher loadings of the hydrophilic active or biologic than can be achieved by simple double emulsion techniques which have been described previously in the literature. These double emulsion routes suffer from burst release at high loadings of the active in the matrix formulation.

Post Processing

Other post processing steps may also be carried out on the particles. Ligands may be conjugated to the surface of the particles. For uncoated particles, ligands are conjugated to the more non-polar blocks of the copolymer. Depending on ligand size, conjugation may occur before or after particle formation. For coated particles, ligands are conjugated to the hydrophilic blocks of the coating amphiphilic copolymer. Depending on ligand size, conjugation may occur before or after particle coating.

Particles may be freeze dried into a stable powder form. Particles may be centrifuged out of solution and re-suspended in a new solvent in which they are still stable. Particles may be dialyzed to change the solvent in which they are suspended or to remove small molecules.

Particles may be administered to a patient by any one of a variety of manners or a combination of varieties of manners. For example, particles may be administered orally, nasally, intraperitoneally, or parenterally, by intravenous, intramuscular, topical, or subcutaneous routes, or by injection into tissue. The particles may be administered in a pharmaceutically acceptable vehicle or carrier.

EXAMPLES

Example 1: Particle Assembly and Morphology

To produce particles containing hydrophilic compounds, poly(n-butyl acrylate) 7.5 kDa-b-poly(acrylic acid) 5.5 kDa (PBA-b-PAA) and the biologic were first dissolved in a polar organic solvent such as DMSO or methanol. In an FNP process, this stream was rapidly mixed with a less polar nonprocess solvent such as chloroform ($CHCl_3$) or acetone in a CIJ mixer. The non-solvent caused the biologic to precipitate. This precipitation was halted by the self-assembly of the hydrophilic PAA block of the PAA-b-PBA on the growing particle surface. The final particles were sterically stabilized in the non-solvent by the hydrophobic PBA block. The resultant nanoparticle had a core-shell structure.

This process has been applied to an assortment of model hydrophilic agents with varying molecular weights, including lysozyme as a model protein (14.3 kDa), the cyclic peptide antibiotic vancomycin (1.45 kDa), a model 7-amino acid long peptide (glycine-arginine-leucine-glycine-tryptophan-serine-phenylalanine (GRLGWSF) [SEQ ID NO 1], 822 Da), the dyes eosin Y (692 Da) and tartrazine (534 Da), the MRI contrast agent gadopentetic acid (548 Da), the aminoglycoside antibiotic tobramycin (468 Da), glutathione (307 Da), and tryptophan (204 Da). Each formulation resulted in nanoparticles with low polydispersities at a minimum loading of 50 wt %.

Example 2: Nanoparticle Loading and Size Control

The sizes of particles produced with FNP may be controlled through the time scales for precipitation of the core material, as well as through the time scale for polymer self-assembly. These time scales are modulated through material concentrations as well as through the choice of nonprocess solvent.

Increasing the percentage of core material necessitated the formation of larger particles. For both lysozyme and vancomycin, the particle size initially decreased as biologic was added compared to the micelle size of the block copolymer. This may be because the addition of core material allows the PAA to more tightly pack due to charge shielding effects. Very high loadings of both lysozyme and vancomycin were obtained. Loading of lysozyme as high as 75 wt % was obtained without the formation of large precipitates, however, the particles were too large to analyze using dynamic light scattering (DLS). Vancomycin loadings up to 90 wt % resulted in stable particles, with sub-100 nm particles observed for loadings below 80 wt %. These loadings indicated that, despite its high water solubility and poor solubility in chloroform, vancomycin played a role in stabilizing the surface—most likely through its aromatic groups.

Additional process variables that were found to impact the particle size included the total mass concentration of polymer and biologic in the DMSO stream, the volume fraction of acetone in the chloroform stream, and the volume fraction of water in the DMSO stream. The addition of 5 vol % water in the DMSO stream reduced the size of the 50% loaded lysozyme particles from 125 nm to 45 nm. With the proper formulation parameters, nanoparticles with loadings greater than 50 wt % and diameters less than 100 nm were readily accessible with the FNP process. By choosing a nonprocess solvent in which the biologic is negligibly soluble the particles may have a very high (>90%) encapsulation efficiency.

Example 3: Stabilization of Nanoparticles for Further Processing

In order to stabilize the nanoparticles in aqueous environments and reduce the loss of encapsulated material during processing steps, methods of crosslinking the PAA shell in order to form a gel were investigated. Ionic crosslinking was focused on because it reduces the risk of covalently modifying the encapsulated agent. The anionic PAA side groups may be crosslinked either with multivalent metal cations or polyamines (S. Bontha, A. V. Kabanov, T. K. Bronich, Polymer micelles with cross-linked ionic cores for delivery of anticancer drugs, J. Controlled Release. 114 (2006) 163-174; T. K. Bronich, A. V. Kabanov, V. A. Kabanov, K. Yu, A. Eisenberg, Soluble Complexes from Poly(ethylene oxide)-block-polymethacrylate Anions and N-Alkylpyridinium Cations, Macromolecules. 30 (1997) 3519-3525; T. K. Bronich, P. A. Keifer, L. S. Shlyakhtenko, A. V. Kabanov, Polymer Micelle with Cross-Linked Ionic Core, J. Am. Chem. Soc. 127 (2005) 8236-8237; R. T. Patil, T. J. Speaker, Retention of trypsin activity in spermine alginate microcapsules, J. Microencapsul. 14 (1997) 469-474). The nanoparticles were successfully stabilized by including chloride salts of $Ca^{2+}$, $Zn^{2+}$, or $Fe^{3+}$ in the nonprocess solvent stream. Spermine, which contains two primary and two secondary amines, and the positively charged antibiotic tobramycin also stabilized the particles. Ionic gelation agents can be added to the nanoparticle solution after the FNP process.

Iron III chloride, included at a 3:1 ratio of acid groups to iron, was an especially effective crosslinking agent. Particles loaded with 50 wt % vancomycin and crosslinked with iron swelled minimally from 72 nm in $CHCl_3$ to 79 nm in methanol, which dissolves non-crosslinked nanoparticles. The minimum swelling indicated a small mesh size, which is necessary to slow the release of encapsulated biologics. For example, the minimal swelling in methanol indicated tight crosslinking. The iron provided enough electron contrast to allow for TEM imaging of the nanoparticles. A TEM micrograph of 20-40 nm particle cores supported the DLS data, which gave larger sizes because the measurement included the PBA shell.

Example 4: Coating Nanoparticles with PEG: Layer-by-Layer FNP

In order to produce nanoparticles that were sterically stabilized in aqueous media, the 50 wt % vancomycin particles stabilized with iron were coated with PEG. The particles were suspended in acetone with one mass equivalent of polystyrene 1.6 kDa-b-poly(ethylene glycol) 5 kDa (PS-b-PEG). This stream was rapidly mixed with water in a second FNP step. The PS block of the PS-b-PEG assembled on the collapsed PBA surface of the particles. Without the PEG, the collapsed hydrophobic PBA surface of the vancomycin nanoparticles caused them to aggregate in water. The final PEG-stabilized particles were 85 nm with no visible aggregates and a near neutral zeta potential. The final nanoparticle structure was a tightly crosslinked hydrogel interior coated in a hydrophobic interface and sterically stabilized by a PEG brush.

The PEG-coated particles had an encapsulation efficiency of 40% (determined by high-pressure liquid chromatography) and a final vancomycin loading of 11.5 wt %. Vancomycin is poorly soluble in chloroform and acetone, so the loss of material likely occurred in the coating step. Because vancomycin has hydrophobic sections that played a role in stabilizing the particle surface in chloroform, it may not have been fully entrapped in the iron-PAA mesh.

Example 5: Nanoparticles Formed with Various Encapsulated Materials

Nanoparticles (NPs) with encapsulated hydrophilic model active pharmaceutical agents (APIs) were created using Flash NanoPrecipitation (FNP) using a confined impingement jets mixer (CIJ) which has been described previously. Generally, the stabilizing polymer (PBA-b-PAA) and API were dissolved in a more polar organic solvent, typically consisting of MeOH or DMSO. This stream was rapidly mixed with an equal volume stream of a more nonpolar anti-solvent at equal flowrates, typically consisting of $CHCl_3$ or acetone. The outlet stream of the CIJ was collected in a stirring bath of antisolvent such that the final nanoparticle solution is 90 vol % antisolvent. outlines the formulations used in this study.

For crosslinked NPs, the crosslinking agent was included in the antisolvent stream such that the charge ratio (ratio of acid groups on the PAA to positive charge of crosslinking agent) was 1:1.

Figures 3A, 3B:
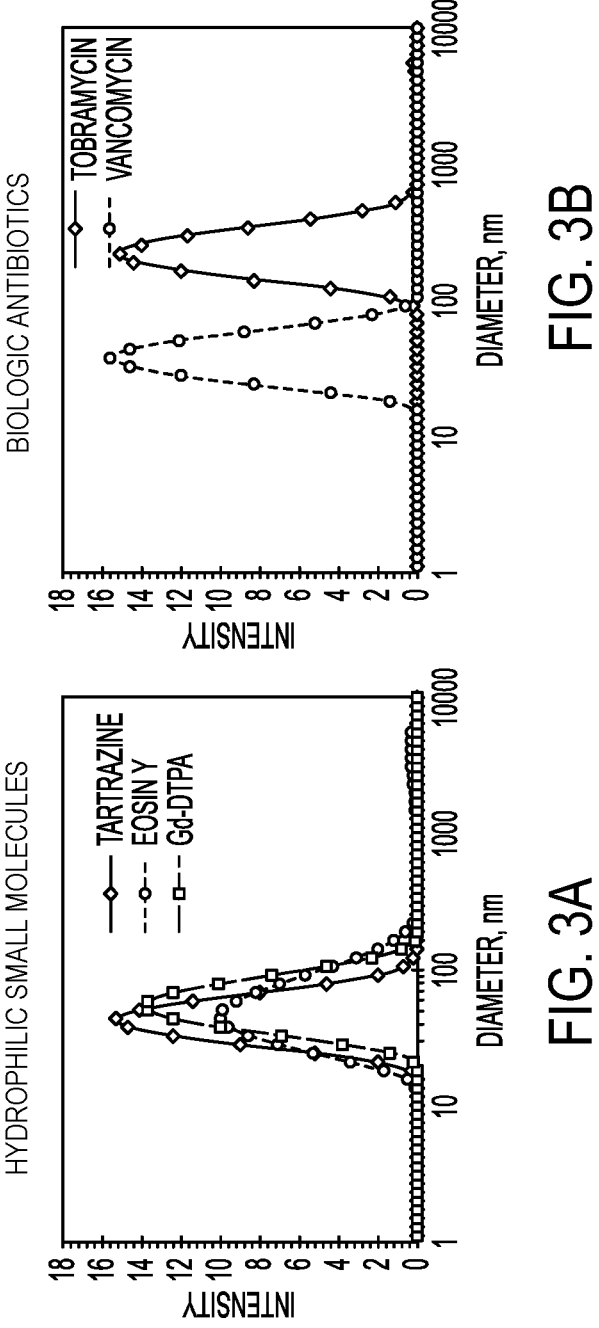
FIGS. 3A, 3B, 3C, and 3D show the particle size distribution for sets of nanoparticles formed that encapsulate various water soluble agents.

Nanoparticles with a hydrophilic core ("inverse" nanoparticles) were formed that encapsulated the small molecules tartrazine, eosin Y, and gadolinium-diethylene triamine pentaacetic acid (Gd-DTPA). The particle size distribution for the sets of particles formed with these encapsulated materials is shown in FIG. 3A.

Nanoparticles with a hydrophilic core were formed that encapsulated the biologic antibiotics tobramycin and vancomycin. The particle size distribution for the sets of particles formed with these encapsulated materials is shown in FIG. 3B.

Figures 3C, 3D:
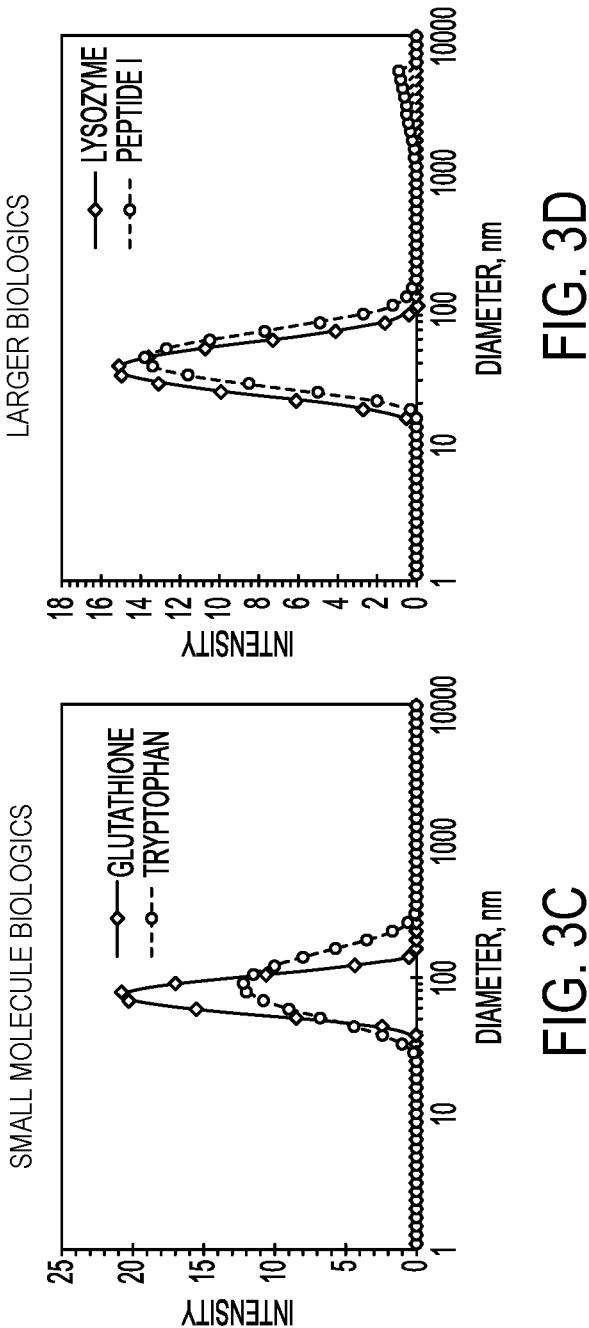

Nanoparticles with a hydrophilic core were formed that encapsulated the small molecule biologics glutathione and tryptophan. The particle size distribution for the sets of particles formed with these encapsulated materials is shown in FIG. 3C.

Nanoparticles with a hydrophilic core were formed that encapsulated the larger biologics lysozyme and "Peptide I" (glycine-arginine-leucine-glycine-tryptophan-serine-phenylalanine (GRLGWSF) [SEQ ID NO 1]). The particle size distribution for the sets of particles formed with these encapsulated materials is shown in FIG. 3D.

The experimental conditions used for the above-described encapsulation systems are provided in Table 2, below.

TABLE 2

| Sample | Process Stream | Nonprocess Stream | Bath |
|---|---|---|---|
| Lysozyme | 500 uL DMSO, 5 mg/mL lysozyme, 5 mg/mL polymer | 500 uL $CHCl_3$ | 4.5 mL $CHCl_3$ |
| Vancomycin | 500 uL DMSO with 5 vol % MQ, 5 mg/mL lysozyme 5 mg/mL polymer | 500 uL $CHCl_3$ | 4.5 mL $CHCl_3$ |
| pepI | 500 uL DMSO with 5 vol % MQ, 5 mg/mL pepI 5 mg/mL polymer | 500 uL $CHCl_3$ | 4.5 mL $CHCl_3$ |
| Eosin Y* | 500 uL DMSO, | 500 uL $CHCl_3$ | 4.5 mL |

TABLE 2-continued

| Sample | Process Stream | Nonprocess Stream | Bath |
|---|---|---|---|
| | 5 mg/mL Eosin Y, 10 mg/mL polymer | | $CHCl_3$ |
| Tartrazine* | 500 uL DMSO with 5 vol % MQ, 5 mg/mL tartrazine, 10 mg/mL polymer | 500 uL $CHCl_3$ | 4.5 mL $CHCl_3$ |
| Gd-DTPA** | 500 uL DMSO with 5 vol % MQ, 5 mg/mL Gd-DTPA, 5 mg/mL polymer | 500 uL $CHCl_3$ | 4.5 mL $CHCl_3$ |
| Tobramycin | 500 uL DMSO, 10 mg/mL polymer | 500 uL DMSO, 5.5 mg/mL tobramycin (1:1 charge ratio) | 4.5 mL acetone |
| Glutathione | 500 uL DMSO with 5 vol % MQ 5 mg/mL glutathione 5 mg/mL polymer | 500 uL $CHCl_3$ | 500 uL $CHCl_3$ |
| Tryptophan**** | 500 uL DMSO with 5 vol % MQ and 5 vol % acetic acid, 5 mg/mL tryptophan, 5 mg/mL polymer | 500 uL $CHCl_3$ | 4.5 mL $CHCl_3$ |

*PBA(3 kDa)-b-PAA(12 kDa) used in these formulations, all others used PBA(7.5 kDa)-b-PAA(5.5 kDa)
**API is first dissolved in MQ (Milli-Q purified water) then diluted with DMSO
****API is first dissolved in acetic acid, then diluted with DMSO Among these encapsulated materials, the smallest encapsulated molecule had a molecular weight of 186 Da, and the largest encapsulated molecular had a molecular weight nearly two order of magnitude greater, 14 kDa, demonstrating the versatility of this process. The encapsulated particles also had a range of charges, for example, tartrazine is negatively charged, whereas tobramycin is positively charged.

A person of skill in the art would appreciate that systems for encapsulating materials can be optimized to determine the best polar process solvent (e.g., DMSO vs. MeOH, optionally with additives), nonprocess solvent (antisolvent) (e.g., acetone, $CHCl_3$, toluene, or DCM), polymer/core material ratios, and/or water content of the solvent stream.

Example 6: PAA-b-PBA Nanoparticles

Poly(acrylic acid)-b-poly(n-butyl acrylate) (12 kDa-b-3 kDa) was dissolved in methanol at a concentration of 20 mg/mL. Basic chromium acetate was dissolved in methanol at a mass concentration of 90 mg/mL. The solutions were mixed one part polymer solution to one part chromium solution by volume. Immediately after the mixture was prepared, it was mixed 1:1 against a chloroform stream in a handheld confined impingement jet (CIJ) mixer. The effluent of the CIJ mixer was collected in a rapidly stirring bath of chloroform such that the final solvent composition was 1 part methanol to 9 parts chloroform by volume. The particles were mixed for 4 days to allow the chromium cations to crosslink the poly(acrylic acid). The resulting particles were 135 nm in chloroform with a polydispersity index (PDI) less than 0.1. Swollen in methanol, the resulting particles were 190 nm with a PDI less than 0.1. Particle diameter was measured by dynamic light scattering using a Malvern Zetasizer in normal analysis mode.

Example 7: Coating of PAA-b-PBA Nanoparticles with PS-b-PEG

The particles from Example 6 were diluted with acetone and centrifuged out of solution at 15000 rcf for 15 minutes.

The supernatant was decanted and the pellet was resuspended in acetone. The particles were centrifuged out of solution a second time at 15000 rcf for 15 minutes. The supernatant was decanted and the pellet was resuspended in acetone to a final mass concentration of 6 mg/mL. Polystyrene-b-poly(ethylene glycol) (1.6 kDa-b-5 kDa) was dissolved in THF at a mass concentration of 12 mg/mL. The particle solution and block copolymer solution were mixed one to one by volume, and then it was mixed 1:1 against a deionized water stream in a handheld confined impingement jet (CIJ) mixer. In deionized water the resulting particles were 195 nm in diameter with a PDI of 0.1 as measured by dynamic light scattering using a Malvern Zetasizer in normal analysis mode.

Example 8: PAA-b-PBA Nanoparticles with Glutathione

Poly(acrylic acid)-b-poly(n-butyl acrylate) (12 kDa-b-3 kDa) was dissolved in methanol at a concentration of 40 mg/mL. Reduced glutathione (GSH) was dissolved in a 1:4 mixture (volume to volume) water and methanol at a mass concentration of 20 mg/mL. Basic chromium acetate was dissolved in methanol at a mass concentration of 90 mg/mL. The solutions were mixed one part polymer solution to one part chromium solution to two parts glutathione solution by volume. Immediately after the mixture was prepared, it was mixed 1:1 against a chloroform stream in a handheld confined impingement jet (CIJ) mixer. The effluent of the CIJ mixer was collected in a rapidly stirring bath of chloroform such that the final solvent composition was 1 part water to 9 parts methanol to 90 parts chloroform by volume. The particles were mixed for 4 days to allow the chromium cations to crosslink the poly(acrylic acid). The resulting particles were 110 nm in chloroform with a PDI less than 0.1. Swollen in methanol, the resulting particles were 130 nm with a PDI less than 0.1. Particle diameter was measured by dynamic light scattering using a Malvern Zetasizer in normal analysis mode.

Example 9: Coating of Glutathione-Containing PAA-b-PBA Nanoparticles with PS-b-PEG The particles from Example 8 were diluted with acetone and centrifuged out of solution at 15000 rcf for 15 minutes. The supernatant was decanted and the pellet was resuspended in acetone. The particles were centrifuged out of solution a second time at 15000 rcf for 15 minutes. The supernatant was decanted and the pellet was resuspended in acetone to a final mass concentration of 6 mg/mL. Polystyrene-b-poly(ethylene glycol) (1.6 kDa-b-5 kDa) was dissolved in THF at a mass concentration of 12 mg/mL. The particle solution and block copolymer solution were mixed one to one by volume, and then it was mixed 1:1 against a deionized water stream in a handheld confined impingement jet (CIJ) mixer. In deionized water the resulting particles were 160 nm in diameter with a PDI of 0.1 as measured by dynamic light scattering using a Malvern Zetasizer in normal analysis mode.

Example 10: PAA-b-PEG Nanoparticles with Glutathione

Poly(acrylic acid)-b-poly(ethylene glycol) (5 kDa-b-5 kDa) was dissolved in methanol at a concentration of 40 mg/mL. Reduced glutathione was dissolved in a 1:4 mixture (volume to volume) water and methanol at a mass concentration of 20 mg/mL. Basic chromium acetate was dissolved in methanol at a mass concentration of 56 mg/mL. The solutions were mixed one part polymer solution to one part chromium solution to two parts glutathione solution by volume. Immediately after the mixture was prepared, it was mixed 1:1 against a chloroform stream in a handheld confined impingement jet (CIJ) mixer. The effluent of the CIJ mixer was collected in a rapidly stirring bath of chloroform such that the final solvent composition was 1 part water to 9 parts methanol to 90 parts chloroform by volume. The particles were mixed for 4 days to allow the chromium cations to crosslink the poly(acrylic acid). The particles were diluted with acetone and centrifuged out of solution at 15000 rcf for 15 minutes. The supernatant was decanted and the pellet was resuspended in acetone. The particles were centrifuged out of solution a second time at 15000 rcf for 15 minutes. The supernatant was decanted and the pellet was resuspended in deionized water. The resulting particles were 245 nm in diameter with a PDI of 0.35 or lower, as measured by dynamic light scattering using a Malvern Zetasizer in normal analysis mode.

Example 11

In a silanized vial, a solution of PS-b-PEG in acetone was added to coat PBA-b-PAA nanoparticles encapsulating vancomycin such that the mass ratio in solution was 2:1:1 PS-b-PEG to PBA-b-PAA to vancomycin. This solution was rotovapped to a total mass concentration of 5 mg/mL. The nanoparticle solution was then diluted ten-fold with acetone and then rotovapped back to a mass concentration of 5 mg/mL five times to ensure all chloroform had been removed.

The nanoparticle and PS-b-PEG solution were mixed at a 1:1 volume ratio with Milli-Q purified water (MQ) in a CIJ and the exit stream was collected in a stirring bath of MQ such that the final solution was 90 vol % MQ. The process stream included 500 μL of 50 vol % DMSO, 45 vol % MeOH, and 5 vol % MQ, with 5 mg/mL of vancomycin and 5 mg/mL of polymer. The nonprocess stream included 600 μL of $CHCl_3$ and 50 μL of $FeCl_3$ (crosslinking agent) in MeOH. The bath included 4.5 mL of $CHCl_3$.

Figure 4:
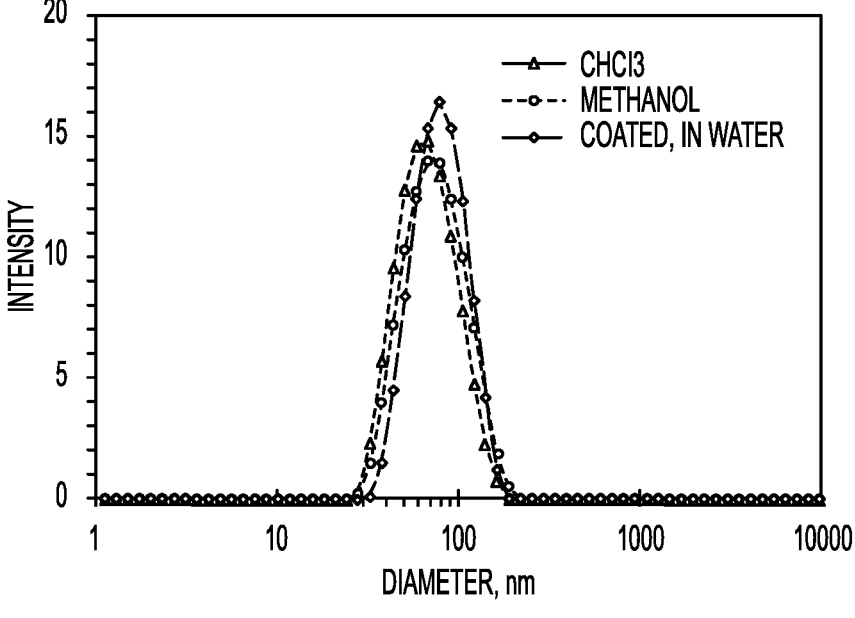
FIG. 4 shows particle size distributions for uncoated particles in chloroform ($CHCl_3$), uncoated particles in methanol (MeOH), and coated particles in water.

The resulting particle sizes are shown in FIG. 4 for uncoated particles in $CHCl_3$, uncoated particles in MeOH, and coated particles in water.

Hydrophobic polymer scaffolds, for example, those based on PLGA, can produce particles capable of peptide and protein release over time scales greater than 1 month. Producing PLGA microparticles with high loading, high encapsulation efficiency, and controlled release can require the formation of a very fine and stable primary emulsion containing a high concentration of biologic. FNP can be used to encapsulate of biologics at loadings greater than 50 wt % in nanoparticles less than 100 nm in diameter, much smaller than the pores produced in most double emulsion methods. The FNP process is scalable and tunable—particles ranging from 40 nm to 300 nm were produced. The resulting particles are sterically stabilized in polar organic solvents by a hydrophobic polymer shell. The anionic core has been crosslinked with multivalent cations and with polyamines. These particles may be incorporated into PLGA scaffolds in order to form a nanocomposite material. The crosslinked hydrogel core can both increase overall encapsulation efficiency by reducing active pharmaceutical ingredient (API) loss to the outside aqueous phase during the final emulsification step, and provide an additional barrier to prolong the release of the therapeutic and decrease the burst release. The dense hydrophobic polymer brush can prevent coalescence and reduce channel formation, increasing the tortuosity of the final PLGA microparticles. A PAA block can protect the biologic from adsorption on the PLGA surface within the pore. The gels formed are nano-scale.

FNP can be used to formulate biologics in polymeric particles for drug delivery. A delivery system can be tailored to optimize its biocompatibility. For example, stabilizing materials can include PLA (to replace the PBA) and a biocompatible anionic polymer (to replace the PAA). Hyaluronic acid, poly(aspartic acid), and poly(glutamic acid) are all possible biodegradable alternatives to the PAA. The process can be optimized to maintain the stability of biologics with more sensitive high levels of structure.

The references cited herein are incorporated by reference in their entirety as if fully set forth herein.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

---

SEQUENCE LISTING

```
Sequence total quantity: 1
SEQ ID NO: 1          moltype = AA   length = 7
FEATURE               Location/Qualifiers
source                1..7
                      mol_type = protein
                      organism = Synthetic Construct
SEQUENCE: 1
GRLGWSF                                                    7
```

---

The invention claimed is:

1. A nanoparticle comprising:
a core comprising a more polar region of a linear copolymer and a water-soluble agent,
a shell comprising a less polar region of the linear copolymer, and
a coating,
wherein the more polar region of the linear copolymer comprises a peptide,
wherein the coating comprises an inner region and an outer region,
wherein the inner region comprises a hydrophobic region of an amphiphilic polymer, and
wherein the outer region comprises a hydrophilic region of the amphiphilic polymer.

2. The nanoparticle of claim 1, wherein the linear copolymer is a diblock copolymer.

3. The nanoparticle of claim 1, wherein the linear copolymer consists of a hydrophilic block coupled with a hydrophobic block.

4. The nanoparticle of claim 1, wherein the more polar region of the linear copolymer comprises an anionic more polar region.

5. The nanoparticle of claim 1, wherein the more polar region comprises poly(glutamic acid), poly(aspartic acid), or a combination.

6. The nanoparticle of claim 1, wherein the more polar region of the linear copolymer comprises a cationic more polar region.

7. The nanoparticle of claim 1, wherein the more polar region comprises polylysine, polyarginine, or a combination.

8. The nanoparticle of claim 1, wherein the more polar region is a poly(amino acid).

9. The nanoparticle of claim 1, wherein the more polar region is a polypeptide.

10. The nanoparticle of claim 1, wherein the linear copolymer is biodegradable.

11. The nanoparticle of claim 1, wherein the less polar region comprises poly(lactic acid) (PLA), poly(glycolic acid), poly(lactic-co-glycolic acid) (PLGA), poly(caprolactone) (PCL), or a combination.

12. The nanoparticle of claim 1,
wherein the copolymer is a block copolymer,
wherein the more polar region of the copolymer consists of poly(glutamic acid) and/or poly(aspartic acid), and
wherein the less polar region of the copolymer consists of poly(lactic acid) (PLA) or poly(lactic-co-glycolic acid) (PLGA).

13. The nanoparticle of claim 1, wherein the nanoparticle has an average size of at least 50 nm and at most 200 nm.

14. The nanoparticle of claim 1, wherein the more polar region of the copolymer in the core is crosslinked.

15. The nanoparticle of claim 1, wherein the water-soluble agent is selected from the group consisting of a biologic material, an amino acid, a peptide, a protein, DNA, RNA, a saccharide, glutathione, tryptophan, a lysozyme, glucagon-like peptide-I (GLP-1), a water-soluble small molecule therapeutic, tobramycin, vancomycin, an imaging agent, eosin, eosin Y, tartrazine, a metal chelate, a gadolinium chelate, and gadolinium diethylene triamine pentaacetic acid (GD-DTPA).

16. The nanoparticle of claim 1, wherein the amphiphilic polymer of the coating is selected from the group consisting of a block copolymer, a diblock copolymer, a triblock copolymer, and a multiblock copolymer.

17. The nanoparticle of claim 1, wherein the amphiphilic polymer of the coating is selected from the group consisting of poly(lactic acid)-block-poly(ethylene glycol) (PLA-b-PEG), poly(lactic-co-glycolic acid)-block-poly(ethylene glycol) (PLGA-b-PEG), and poly(ethylene oxide)-block-poly(propylene oxide)-block-poly(ethylene oxide) (PEO-b-PPO-b-PEO).

18. The nanoparticle of claim 1, wherein the amphiphilic polymer of the coating is a polyethylene glycol-lipid (PEG-lipid).

19. The nanoparticle of claim 1, wherein the less polar region of the linear copolymer comprises poly(n-butyl acrylate) (PBA).

20. A method of treating a cancer or AIDS, comprising administering the nanoparticle of claim 1 to a patient suffering from the cancer or the AIDS, wherein the water-soluble agent is capable of treating the cancer or the AIDS.

* * * * *